United States Patent [19]

Thorens

[11] Patent Number: 5,670,360
[45] Date of Patent: Sep. 23, 1997

[54] MAMMALIAN RECEPTORS FOR GLUCAGON-LIKE-PEPTIDE-1 (GLP-1), CORRESPONDING DNA AND RECOMBINANT EXPRESSION SYSTEMS, AND SCREENING ASSAYS FOR GLP-1 AGONISTS AND ENHANCERS

[75] Inventor: Bernard Thorens, Epalinges, Switzerland

[73] Assignee: Novo Nordisk A/S, Bagsvaerd, Denmark

[21] Appl. No.: 142,439

[22] PCT Filed: Mar. 23, 1993

[86] PCT No.: PCT/EP93/00697

§ 371 Date: Nov. 24, 1993

§ 102(e) Date: Nov. 24, 1993

[87] PCT Pub. No.: WO93/19175

PCT Pub. Date: Sep. 30, 1993

[30] Foreign Application Priority Data

Mar. 25, 1992 [DK] Denmark ................................. 398/92

[51] Int. Cl.⁶ ..................... C07K 14/72; C12N 15/12; C01N 33/53
[52] U.S. Cl. ................. 435/240.2; 435/7.1; 435/7.21; 435/69.1; 435/320.1; 435/252.3; 435/254.11; 530/350; 536/23.5
[58] Field of Search ....................... 530/350, 395; 536/23.5; 435/7.1, 69.1, 240.2, 320.1, 252.3, 254.11, 7.21

[56] References Cited

PUBLICATIONS

Richter et al., FEBS Letters, vol. 267, No. 1, pp. 78–80 (1990).

Uttenthal et al., FEBS Letters, vol. 262, No. 1, pp. 139–141 (1990).

Thorens, Proc. Natl. Acad. Sci., vol. 89, No. 18, pp. 8641–8645 (1992).

Saxena, B. B., et al. (1986) *Biochem.* 25: 7943–50.

Jüppner, H., et al. (1991) *Science* 254: 1024–26.

Lin, H. Y., et al. (1991) *Science* 254: 1022–24.

Göke et al. (1992) *FEBS Lett.* 300(3): 232–36.

Lankat-Buttgerett, B., et al. (1994) *Exp. Clin. Endocrinol.* 102: 341–347.

Watson, S., et al. (1994) *The G–Protein Linked Receptor Facts Book*, London: Academic Press, pp. 128–129.

*Primary Examiner*—David L. Fitzgerald
*Attorney, Agent, or Firm*—Steve T. Zelson, Esq.; James J. Harrington, Esq.

[57] ABSTRACT

The present invention relates to a recombinant glucagon like peptide-1 (GLP-1), to a DNA construct which comprises a DNA sequence encoding a GLP-1 receptor, to methods of screening for agonists of GLP-1 activity, and to the use of the GLP-1 receptor for screening for agonists of GLP-1 activity.

11 Claims, 8 Drawing Sheets

GLPR  MAVTP----SLLR----LALLLLGAVGRAGPAPQGA------------------TVSLSETVQKWREYRHQCQRFLTE---------
SECR  NLSTMAPR-LSLLL----LRLLLLTKAAHTV---GV--------------------PPRLCDVRRVLLEERAHCLQQLSKEK------
PTHR  MGAPRISHSLALLLCCSVLSSVYALVDADDVITKEEQIILLANAQAQCEQELKEVLRVPELAESAKDMSRSAKTKEKPAEKLYPQAEE-
CTRI  MRFTLTRVCLTLFIFLNRPLPULPDSADGAHTPTLEPEPFLY-----------LEAQHRC----------------Y-----D

GLPR  -----APLLATGLF—NRTFDDYA—UPDGPPGSFUNUS—PWYLPWASSULQGHVYRF—TAEGIULHKDNSSLPWRDLSECEESKQGERNSP   137
SECR  -KGALGPETASG---EGLWDNS—UPSSAPARTVEURC—PKSLLSLSNK-NGSLFRH—TQDG-W-----SETFPRPDLACGVNINNSFNERR   135
PTHR  SREUSDASRLQDGF—PEWDNIV—UPAGUPGKUVARUP—DYFYDFNHK--GAVAR—PDYFPDFDA--AEKVTKY—EOQDVAHPESNISVSHYTMCNAFTP--DKLQ  178
CTRI  ANQKLPPYQGEGLY—NATWDGWS—UDDTPAGULAEQY—CPDYFPDFDA--AEKVTKY—EOQDVAHPESNISVSHYTMCNAFTP--DKLQ  144

GLPR  EEQLLSLYIIYTUGYALSFSALVIASRAILUSFRAHLHCTANYIHLNLFASFILRALSUFIKDAALKWNYSTAAQQHQUDG--LLSY--QDS-       223
SECR  HAYLLKLKWNYTUGYSSSLAMLLVALSILCSFARLHCTANYIHNHLFUSFILRALSNFIKDAVL---FSSDD---------UTYCQAHK-          212
PTHR  EV-FDRLGMIYTUGYSISLGSLTVARULILGYFRAHLCTRNYIHMHLFUSFMLRAVSIFIKDAVLYSGVSTDEIERITEELRAFTEPPPA         267
CTRI  NAYI--LYYLAIUGHSLSILTLLISLGIFMFLRSISCQRVTLHKNAFLTYULNSIIIIUHLVVI-------UPNGELUK-RDPPI-              219
```

FIG. 1B

```
                    III                                                                                IV
GLPR  ----LGCALVFLLLNQYCUANYYVLVEGUYLYTILLAFSUFSEQRIFKLYLSIGVGUPLLFUIPVGIVKYLYEDEGCVTANSNNYVLI    308
SECR  ----VGCKLVHIFFQYCINANYAVLLVEGLYLHTLLAISFFSERKYLQAFVLLGVGSPAIFVALVAITANFLENTGCVDINANASVHHV    297
PTHR  DKAGFVGCRVAVTUFLYFLTTHYYHILVEGLYLHSLIFNAFFSEKKYLVGFTLFGVGLPAVFVAVUTURATLANTECHDLSSGHKKV-I    356
CTR1  ----CKVLHFFHQYNMSCNYFWMLCEGVYLHTLIVVSVFAEGQRLWMYHVLGUGFPLIPTTAHAITRANLFNDNCW-LSVDTNLLYI       301
                  *    **        . . . *  . *. ** .    . *. . ..   .:.   . . *
                V                                                                                    VI
GLPR  IRLPILFAIGVNFLVFIAVICIVIAKLKANLMCKTDIKC---ALAKSTLTLIPLLGTHEVIFAFVMDEHARGTLAFUKLFTELSFTSFQG   395
SECR  IRGPVILSILINFIFFINILRILMRKLATQETAGSETNH-YKALAKSTLLLIPLFGIHYIVAFSHEDAME-----VQLFFELALGSFQG   381
PTHR  IQUPILAIVUNFILFINIIRVLATKLRETNAGRCDTAQQYRKLLKSTLVLMPLFGVHYIVFMATPYTEVSGILVQQMHYENLFNSFQG    446
CTR1  IHGPVNAALVVHFFFLLNILAVLVUKKLKLKESQE---AESHMYLKAVAATLILVPLLGVQFUVLPWRPSTPLLGKIYD---YVVHSLIHFQG  385
                           ***    . *. **.*. *. ..   *..
                   VII
GLPR  FNVAVLYCFVNNEVQMEFRKSWERWRLE-ALHIQADSSNKPLKC-----------------------------------
SECR  LVUAVLYCFLNGEVQLEVQLKWRQWHLQ-EFPLRPVAFNNSFSN-----------------------------------
PTHR  FFVAIIYCFCNGEVQAEIKKSWSRWTLALDFKRKARSGSSTYSYGPMVSHTSVTNVGPAGGLALSLSPALAPGAGASANGHHQLPGYVKH   536
CTR1  FFVAIIYCFCNKEVQAEIKKSWSRWTLALDFKRKARSGSSTYSYGPMVSHTSVTNVGPAGGLALSLSPALAPGAGASANGHHQLPGYVKH-EIPVYICH   449
       **  ****  *  *  * .. *.  ***

GLPR  ---------PTSSVSSGATV-------GSSVYAATC---------QNSCS      463
SECR  ---------ATNGPTHSTKA-------STEQSASIP---------RASII      419
PTHR  GSISENSLPSSGPEPGTKDDGYLNGSGLYEPHVGEQPPLLEEERETVA---      585
CTR1  QEPREEP-------AGEEPVVEVEG-----------VEVIANEVLEQE--TSA   482
                                           ..
```

```
RAT  - MAVTPSLLRLALLLLGAVGRAGPRPQGATVSLSETVQKWREYRHQCQRFL  - 50

RAT  - TEAPLLATGLFCNRTFDDYACWPDGPPGSFVNVSCPWYLPWASSVLQGHV  -100

RAT  - YRFCTAEGIWLHKDNSSLPWRDLSECEESKQGERNSPEEQLLSLYIIYTV  -150

RAT  - GYALSFSALVIASAILVSFRHLHCTRNYIHLNLFASFILRALSVFIKDAA  -200
                    ::: ::::::::::::::::::::::::::::::::
HUM  -                RHLYCTRNYIHLNLFASFILRALSVFIKDAA  - 31

RAT  - LKWMYSTAAQQHQWDGLLSYQDSLGCRLVFLLMQYCVAANYYWLLVEGVY  -250
       :::::::::::::::::::::::::::::: :::::::::::::::::::
HUM  - LKWMYSTAAQQHQWDGLLSYQDSLSCRLVFLLMQYCVAANYYWLLVEGVY  - 81

RAT  - LYTLLAFSVFSEQRIFKLYLSIGWGVPLLFVIPWGIVKYLYEDEGCWTRN  -300
       ::::::::::::::: :: :: :::::::::::: :::::: ::::::::
HUM  - LYTLLAFSVFSEQWIFRLYVSIGWGVPLLFVVPWGIVKILYEDEGCWTRN  -131

RAT  - SNMNYWLIIRLPILFAIGVNFLVFIRVICIVIAKLKANLMCKTDIKCRLA  -350
       :::::::::::::::::::::::: : :::::: ::::::::::::::::
HUM  - SNMNYWLIIRLPILFAIGVNFLIFVRVICIVVSKLKANLMCKTDIKCRLA  -181

RAT  - KSTLTLIPLLGTHEVIFAFVMDEHARGTLRFVKLFTELSFTSFQGFMVAV  -400
       :::::::::::::::::::::::::::::::: :::::::::::::: ::
HUM  - KSTLTLIPLLGTHEVIFAFVMDEHARGTLRFIKLFTELSFTSFQGLMVAI  -231

RAT  - LYCFVNNEVQMEFRKSWERWRLERLNIQRDSSMKPLKCPTSSVSSGATVG  -450
       :::::::::: :::::::::::::: :::::::::::::::: ::::: :
HUM  - LYCFVNNEVQLEFRKSWERWRLEHLHIQRDSSMKPLKCPTSSLSSGATAG  -281

RAT  - SSVYAATCQNSCS  -463
       .. :: : :::: :::
HUM  - SSMYTATCQASCS  -294
```

FIG. 7

MAMMALIAN RECEPTORS FOR GLUCAGON-LIKE-PEPTIDE-1 (GLP-1), CORRESPONDING DNA AND RECOMBINANT EXPRESSION SYSTEMS, AND SCREENING ASSAYS FOR GLP-1 AGONISTS AND ENHANCERS

FIELD OF THE INVENTION

The present invention relates to a recombinant glucagon-like peptide-1 (GLP-1) receptor, to a DNA construct which comprises a DNA sequence encoding a GLP-1 receptor, to methods of screening for agonists of GLP-1 activity, and to the use of the GLP-1 receptor for screening for agonists of GLP-1 activity.

BACKGROUND OF THE INVENTION

As used in the present specification the designation GLP-1 comprises GLP-1(7-37) as well as GLP-1(7-36) amide.

Glucose-induced insulin secretion is modulated by a number of hormones and neurotransmitters. In particular, two gut hormones, glucagon-like peptide-1 (GLP-1) and gastric inhibitory peptide (GIP) potentiate the effect of glucose on insulin secretion and are thus called gluco-incretins (Dupre, in The Endocrine Pancreas, E. Samois Ed. (Raven Press, New York, (1991), 253–281) and Ebert and Creutzfeld, (Diabetes Metab. Rev. 3, (1987)). Glucagon-like peptide-1 is a glucoincretin both in rat and in man (Dupre and Ebert and Creutzfeld, vide supra, and Kreymann et al. (Lancet 2 (1987), 1300)). It is part of the preproglucagon molecule (Bell et al. Nature 304 (1983), 368) which is proteolytically processed in intestinal L cells to GLP-1(1-37) and GLP-1(7-36)amide or GLP-1(7-37) (Mojsov et al. (J. Biol. Chem. 261 (1986), 11880) and Habener et al.: The Endocrine Pancreas E. Samois Ed. (Raven Press, New York (1991), 53–71). Only the truncated forms of GLP-1 are biologically active and both have identical effects on insulin secretion in beta cells (Mojsov et al. J. Clin. Invest 79 (1987), 616) and Weir et al. (Diabetes 38 (1989), 338). They are the most potent gluco-incretins so far described and are active at concentrations as low as one to ten picomolar. The stimulatory effect of these gluco-incretin hormones requires the presence of glucose at or above the normal physiological concentration of about 5 mM and is mediated by activation of adenylate cyclase and a rise in the intracellular concentration of cyclic AMP (Drucker et al. Proc. Natl. Acad. Sci. USA 84 (1987), 3434) and Göke et al. (Am. J. Physiol. 257 (1989), G397). GLP-1 has also a stimulatory effect on insulin gene transcription (Drucker et al. Proc. Natl. Acad. Sci. USA 84 (1987), 3434). Non-insulin-dependent diabetes mellitus (NIDDM) is associated with a reduced stimulatory effect of GLP-1 on glucose-induced insulin secretion (Suzuki et al. Diabetes 39 (1990), 1320). In man, in one study, GLP-1 levels were elevated in NIDDM patients both in the basal state and after glucose ingestion; however, following a glucose load there was only a very small rise in plasma insulin concentration (Ørskov et al. J. Clin. Invest. 87 (1991), 415). A recent study (Nathan et al. Diabetes Care 15 (1992), 270) showed that GLP-1 infusion could ameliorate postprandial insulin secretion and glucose disposal in NIDDM patients. Thus, as a further step in understanding the complex modulation of insulin secretion by gut hormones and its dysfunction in diabetes, we isolated and characterized a complementary DNA for the beta cell GLP-1 receptor and showed that it is part of a new family of G-coupled receptors.

DESCRIPTION OF THE INVENTION

The present invention relates to a recombinant glucagon-like peptide-1 (GLP-1) receptor.

More preferably, the invention relates to a GLP-1 receptor which comprises the amino acid sequence shown in SEQ ID No. 1, or an analogue thereof binding GLP-1 with an affinity constant, $K_D$, below 100 nM, preferably below 10 nM. In the present context, the term "analogue" is intended to indicate a naturally occurring variant (including one expressed in other animal species, in particular human) of the receptor or a "derivative" i.e. a polypeptide which is derived from the native GLP-1 receptor by suitably modifying the DNA sequence coding for the variant, resulting in the addition of one or more amino acids at either or both the C- and N-terminal ends of the native amino acid sequence, substitution of one or more amino acids at one or more sites in the native amino acid sequence, deletion of one or more amino acids at either or both ends of the native sequence or at one or more sites within the native sequence, or insertion of one or more amino acids in the native sequence.

In another aspect, the present invention relates to a DNA construct which comprises a DNA sequence encoding the GLP-1 receptor of the invention, as well as a recombinant expression vector carrying the DNA construct and a cell containing said recombinant expression vector.

In one embodiment of the invention, the GLP-1 receptor molecule may be provided in solubilised and/or reconstituted form.

In the present context "solubilised" is intended to indicate a receptor as present in detergent-solubilised membrane preparations. "Reconstituted" is intended to indicate a receptor solubilised in the presence of essential cofactors, e.g. G-protein. In this embodiment the receptor may be in a reconstituted micellar form.

The DNA construct of the invention encoding the GLP-1 receptor preferably comprises the DNA sequence shown in SEQ ID No. 1, or at least a DNA sequence coding for a functional analogue thereof binding GLP-1 with an affinity below 100 nM, preferably below 10 nM or a suitable modification thereof. Examples of suitable modifications of the DNA sequence are nucleotide substitutions which do not give rise to another amino acid sequence of the GLP-1 receptor, but which may correspond to the codon usage of the host organism into which the DNA construct is introduced or nucleotide substitutions which do give rise to a different amino acid sequence and therefore, possibly, a different protein structure without, however, impairing the properties of the native variant. Other examples of possible modifications are insertion of one or several nucleotides into the sequence, addition of one or several nucleotides at either end of the sequence, or deletion of one or several nucleotides at either end or within the sequence.

Another example of a DNA construct of the invention is one which encodes a GLP-1 receptor variant particularly suitable for solubilisation and reconstitution.

The DNA construct of the invention encoding the present GLP-1 receptor may be prepared synthetically by established standard methods, e.g. the phosphoramidite method described by Beaucage and Caruthers, Tetrahedron Letters 22 (1981), 1859–1869, or the method described by Matthes et al., EMBO Journal 3 (1984), 801–805. According to the phosphoramidite method, oligonucleotides are synthesized, e.g. in an automatic DNA synthesizer, purified, annealed, ligated and cloned in suitable vectors.

The DNA construct of the invention may also be of genomic or cDNA origin, for instance obtained by preparing a genomic or cDNA library and screening for DNA sequences coding for all or part of the GLP-1 receptor of the invention by hybridization using synthetic oligonucleotide probes in accordance with standard techniques (cf. Sambrook et al., Molecular Cloning: A Laboratory Manual, 2nd Ed., Cold Spring Harbor, 1989). In this case, a genomic or cDNA sequence encoding the GLP-1 receptor may be modified at a site corresponding to the site(s) at which it is desired to introduce amino acid substitutions, e.g. by site-directed mutagenesis using synthetic oligonucleotides encoding the desired amino acid sequence for homologous recombination in accordance with well-known procedures.

Finally, the DNA construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire DNA construct, in accordance with standard techniques. The DNA construct may also be prepared by polymerase chain reaction using specific primers, for instance as described in U.S. Pat. No. 4,683,202 or Saiki et al., Science 239 (1988), 487–491.

The recombinant expression vector into which the DNA construct of the invention is inserted may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the GLP-1 receptor of the invention should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA encoding the GLP-1 receptor of the invention in mammalian cells are the SV40 promoter (Subramani et al., Mol. Cell Biol. 1 (1981), 854–864), the MT-1 (metallothionein gene) promoter (Palmiter et al., Science 222 (1983), 809–814) or the adenovirus 2 major late promoter. A suitable promoter for use in insect cells is the polyhedrin promoter (Vasuvedan et al., FEBS Lett. 311, (1992) 7–11). Suitable promoters for use in yeast host cells include promoters from yeast glycolytic genes (Hitzeman et al., J. Biol. Chem. 255 (1980), 12073–12080; Alber and Kawasaki, J. Mol. Appl. Gen. 1 (1982), 419–434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4c (Russell et al., Nature 304 (1983), 652–654) promoters. Suitable promoters for use in filamentous fungus host cells are, for instance, the ADH3 promoter (McKnight et al., The EMBO J. 4 (1985), 2093–2099) or the tpiA promoter.

The DNA sequence encoding the GLP-1 receptor of the invention may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) terminators. The vector may further comprise elements such as polyadenylation signals (e.g. from SV40 or the adenovirus 5 E1b region), transcriptional enhancer sequences (e.g. the SV40 enhancer) and translational enhancer sequences (e.g. the ones encoding adenovirus VA RNAs).

The recombinant expression vector of the invention may further comprise a DNA sequence enabling the vector to replicate in the host cell in question. An example of such a sequence (when the host cell is a mammalian cell) is the SV40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hygromycin or methotrexate.

The procedures used to ligate the DNA sequences coding for the GLP-1 receptor of the invention, the promoter and the terminator, respectively, and to insert them into suitable vectors containing the information necessary for replication, are well known to persons skilled in the art (cf., for instance, Sambrook et al., op.cit.).

The host cell into which the expression vector of the invention is introduced may be any cell which is capable of producing the GLP-1 receptor of the invention and is preferably a eukaryotic cell, such as invertebrate (insect) cells or vertebrate cells, e.g. Xenopus laevis oocytes or mammalian cells, in particular insect and mammalian cells. Examples of suitable mammalian cell lines are the COS (ATCC CRL 1650), BHK (ATCC CRL 1632, ATCC CCL 10), CHL (ATCC CCL 39) or CHO (ATCC CCL 61) cell lines. Methods of transfecting mammalian cells and expressing DNA sequences introduced in the cells are described in e.g. Kaufman and Sharp, J. Mol. Biol. 159 (1982), 601–621; Southern and Berg, J. Mol. Appl. Genet. 1 (1982), 327–341; Loyter et al., Proc. Natl. Acad. Sci. USA 79 (1982), 422–426; Wigler et al., Cell 14 (1978), 725; Corsaro and Pearson, Somatic Cell Genetics 7 (1981), 603, Graham and van der Eb, Virology 52 (1973), 456; and Neumann et al., EMBO J. 1 (1982), 841–845.

Alternatively, fungal cells (including yeast cells) may be used as host cells of the invention. Examples of suitable yeasts cells include cells of Saccharomvces spp. or Schizosaccharomyces spp., in particular strains of Saccharomyces cerevisiae. Examples of other fungal cells are cells of filamentous fungi, e.g. Aspergillus spp. or Neurospora spp., in particular strains of Aspergillus oryzae or Aspergillus niger. The use of Aspergillus spp. for the expression of proteins is described in, e.g., EP 272 277.

The GLP-1 receptor according to the invention may be produced by a method which comprises culturing a cell as described above in a suitable nutrient medium under conditions which are conducive to the expression of the GLP-1 receptor, and recovering the GLP-1 receptor from the culture. The medium used to culture the cells may be any conventional medium suitable for growing mammalian cells, such as a serum-containing or serum-free medium containing appropriate supplements. Suitable media are available from commercial suppliers or may be prepared according to published recipes (e.g. in catalogues of the American Type Culture Collection).

If the GLP-1 receptor has retained the transmembrane and (possibly) the cytoplasmic region of the native variant, it will be anchored in the membrane of the host cell, and the cells carrying the GLP-1 receptor may be used as such in the screening or diagnostic assay. Alternatively, the receptor may be a component of membrane preparations, e.g. in solubilised and/or reconstituted form as defined above.

In a still further aspect, the present invention relates to a method of screening for agonists or enhancers of GLP-1 activity, the method comprising incubating a GLP-1 receptor according to any of claims 1–3 with a substance suspected to be an agonist of GLP-1 activity and subsequently with a GLP-1 or an analogue thereof, and detecting any effect from the suspected agonist on the binding of GLP-1 to the GLP-1 receptor. An enhancer being defined as a compound capable of stabilizing interaction between a high-affinity form of the receptor and the corresponding ligand, as described e.g. for the adenosine receptor (Bruns et al. Molecular Pharmacology 38 (1990), 939).

An alternative method of screening for agonists of GLP-1 activity, comprises incubating GLP-1 or an analogue thereof with a substance suspected to be an agonist of GLP-1 activity and subsequently with a GLP-1 receptor of the invention, and detecting any effect on the binding to the GLP-1 receptor. Such agonists of GLP-1 activity will be substances stimulating glucose-induced insulin secretion and may be used in the treatment of NIDDM.

The GLP-1 receptor may be immobilized on a solid support and may, as such, be used as a reagent in the screening methods of the invention. The GLP-1 receptor may be used in membrane-bound form, i.e. bound to whole cells or as a component of membrane preparations immobilised on a solid support.

The solid support employed in the screening methods of the invention preferably comprises a polymer. The support may in itself be composed of the polymer or may be composed of a matrix coated with the polymer. The matrix may be of any suitable material such as glass, paper or plastic. The polymer may be selected from the group consisting of a plastic (e.g. latex, a polystyrene, polyvinylchloride, polyurethane, polyacrylamide, polyvinylalcohol, nylon, polyvinylacetate, and any suitable copolymer thereof), cellulose (e.g. various types of paper, such as nitrocellulose paper and the like), a silicon polymer (e.g. siloxane), a polysaccharide (e.g. agarose or dextran), an ion exchange resin (e.g. conventional anion or cation exchange resins), a polypeptide such as polylysine, or a ceramic material such as glass (e.g. controlled pore glass).

The physical shape of the solid support is not critical, although some shapes may be more convenient than others for the present purpose. Thus, the solid support may be in the shape of a plate, e.g. a thin layer or microtiter plate, or a film, strip, membrane (e.g. a nylon membrane or a cellulose filter) or solid particles (e.g. latex beads or dextran or agarose beads). In a preferred embodiment, the solid support is in the form of wheat germ agglutinin-coated SPA beads (cf. U.S. Pat. No. 4,568,649).

Alternatively, screening for GLP-1 agonists can also be carried out using a cell line expressing the cloned GLP-1 receptor functionally coupled to a G-protein. In living cells, exposure to an agonist will give rise to an increase in the intracellular cAMP concentration. The cAMP concentration can then be measured directly. Changes in cAMP levels may also be monitored indirectly using appropriate cell lines in which a measurable signal is generated in response to an increase in intracellular cAMP.

It is furthermore contemplated to locate the ligand-binding site on the GLP-1 receptor of the invention, for instance by preparing deletion or substitution derivatives of the native GLP-1 receptor (as described above) and incubating these with ligands known to bind the full-length GLP-1 receptor and detecting any binding of the ligand to the GLP-1 receptor deletion derivative. Once the ligand-binding site has been located, this may be used to acquire further information about the three-dimensional structure of the ligand-binding site. Such three-dimensional structures may, for instance, be established by means of protein engineering, computer modelling, NMR technology and/or crystallographic techniques. Based on the three-dimensional structure of the ligand-binding site, it may be possible to design substances which are agonists to the GLP-1 molecule.

The characterization of the GLP-1 receptor is of considerable physiological and pathological importance. It will help study a fundamental aspect of the entero-insular axis (Unger and Eisentraut, Arch. Int. Med. 123 (1969), 261): the potentiating effect of gut hormones on glucose-induced insulin secretion, the role of these hormones in the control of glucose homeostasis and also the possible therapeutic use of GLP-1 to stimulate insulin secretion in NIDDM patients (Mathan et al. Diabetes Care 15 (1992), 270). Investigation of the regulated expression and desensitization of the receptor in the normal state and during the development of diabetes will contribute to a better understanding of the modulation of insulin secretion in normal and pathological situations. Availability of antibodies against this receptor may also allow an analysis of the surface localization of this receptor and its distribution relative to the beta cell glucose transporter GLUT2 (Thorens et al. Cell 55 (1988), 281 and Orci et al. Science 245 (1989), 295). This aspect pertains to the hypothesis that the beta cell membrane has a "regulatory" domain which contains hormone receptors (Bonner-Weir Diabetes 37 (1988), 616), and which may be distinct from GLUT2-containing membrane domains previously identified (Thorens et al. Cell 55 (1988), 281 and Orci et al. Science 245 (1989), 295). Finally, the identification of an additional member of this new family of G-coupled receptors will help design experiments to probe the structure-function relationship of these new molecules.

BRIEF DESCRIPTION OF THE DRAWINGS

The present invention is further illustrated in the following examples with reference to the appended drawings in which FIG. 1A and FIG. 1B (which is a continuation of FIG. 1A) together show the amino acid sequence of the rat GLP-1 receptor in a comparison with the sequence of the rat secretin receptor (SECR), the opossium parathyroid hormone receptor (PTHR) and the porcine calcitonin receptor (CTR1). The GLP-1 receptor has three N glycosylation sites in the extracellular domain (arrows). Four cysteines are conserved at identical places in the four receptor (boxes). Note the otherwise very divergent sequences in this part of the molecules as well as in the COOH-terminal cytoplasmic tail. Sequence identities are denoted by stars and homologies by dots. The location of the putative transmembrane domains are indicated by horizontal bars above the sequences.

Figure 2:
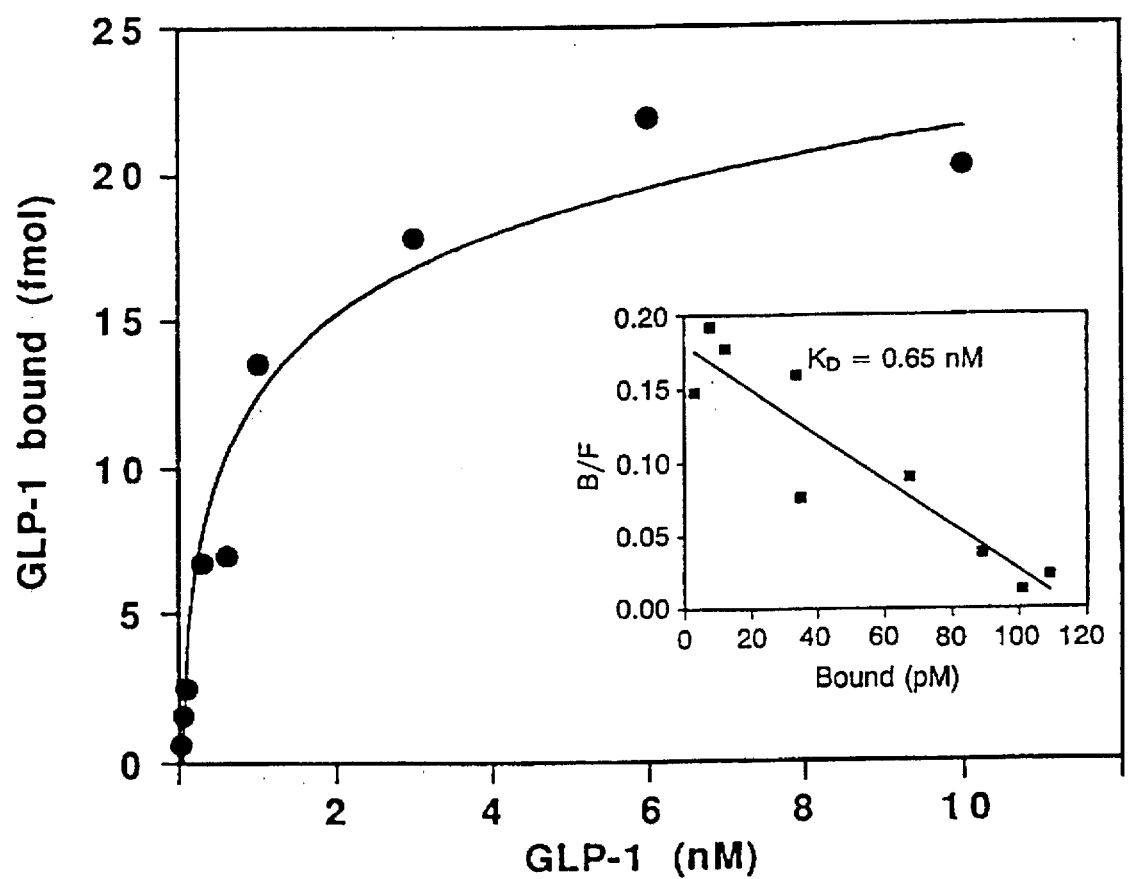
FIG. 2 shows binding of $^{125}$I-GLP-1 to COS cells transfected with the pGLPR-16 plasmid. Specific binding reaches saturation at 1 to 10 nM GLP-1. Insert: Scatchard analysis of GLP-1 binding.
Figure 3:
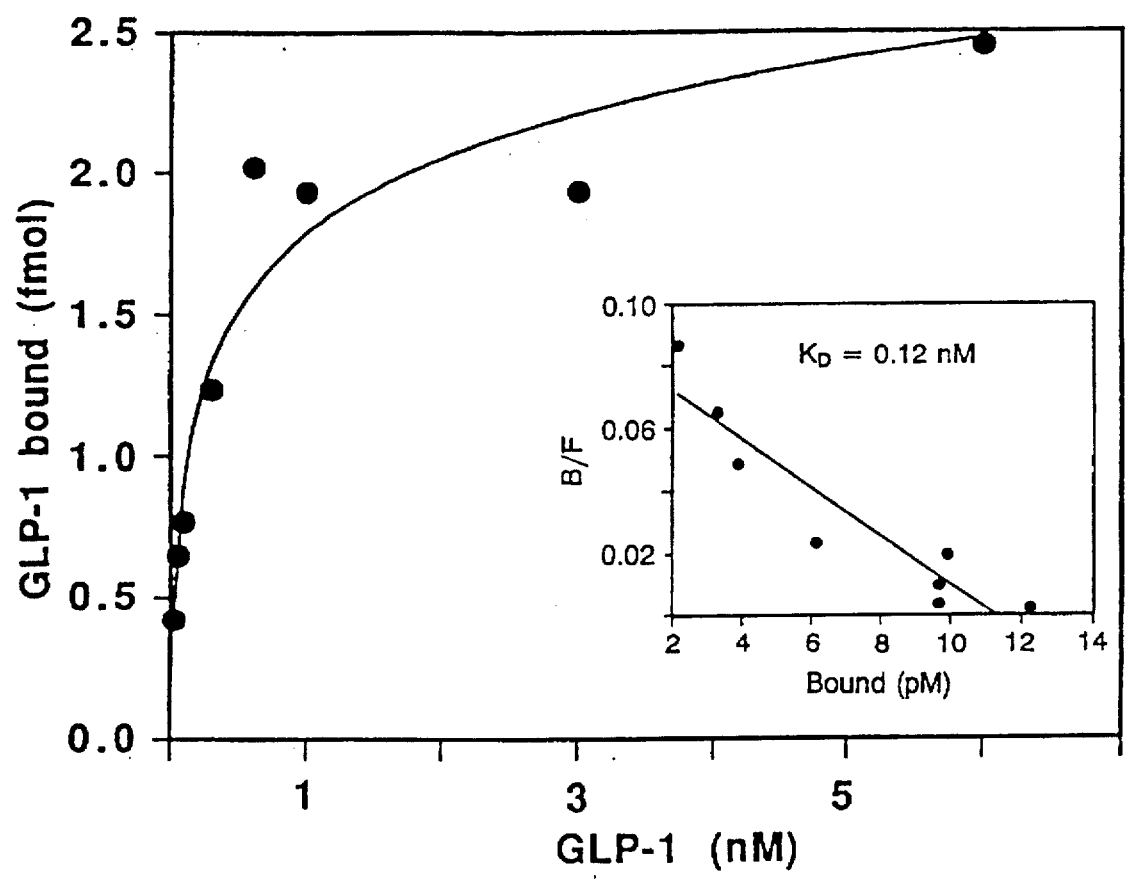
FIG. 3 shows binding of $^{125}$I-GLP-1 to INS-1 cells. Specific binding reaches saturation at 1 to 10 nM GLP-1. Insert: Scatchard analysis of GLP-1 binding.

Fitting of the curves in FIGS. 2 and 3 were performed with the LIGAND program (McPherson, Kinetic, EBDA, Ligand, Lowry. A Collection of radioligand analysis programs (Elsevier, Amsterdam 1985)).

Figure 4:
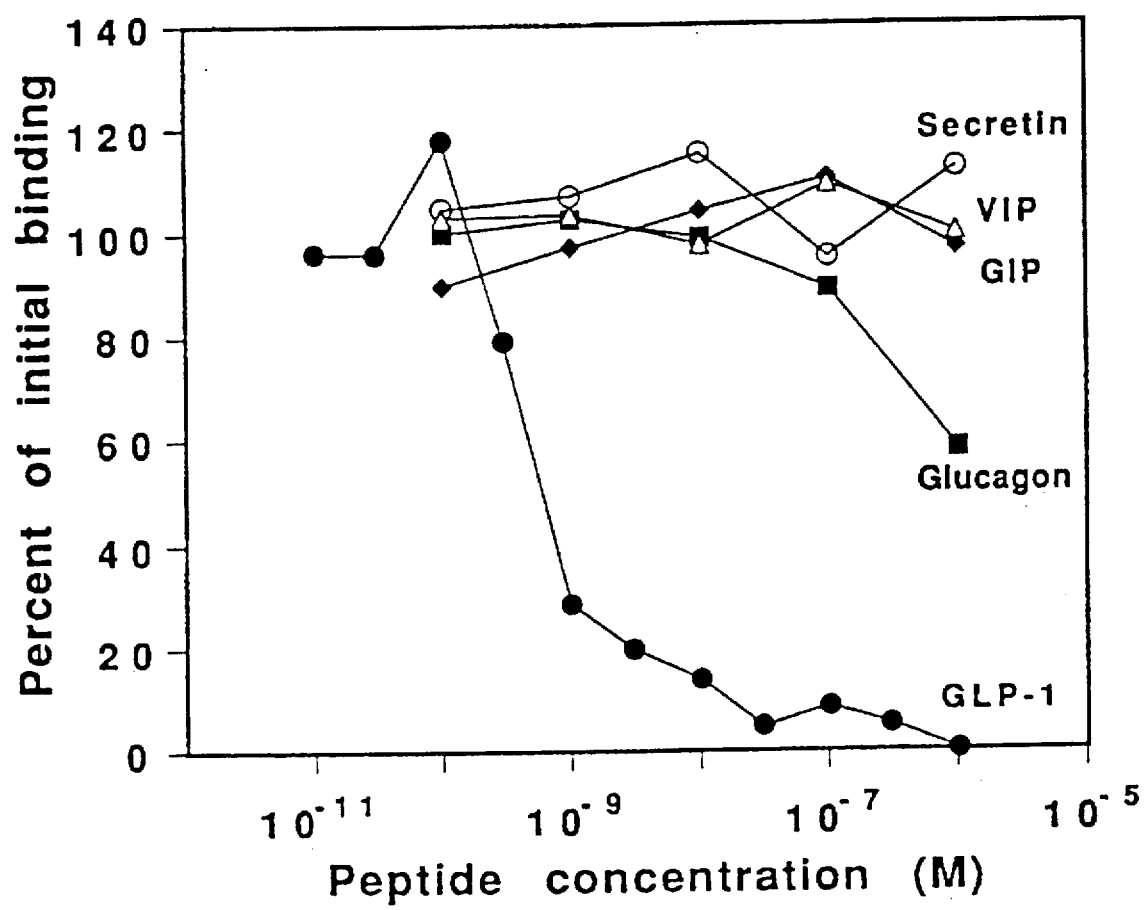

FIG. 4 shows displacement of $^{125}$I-GLP-1 binding to COS cells transfected with the rat GLP-1 receptor cDNA. Transfected cells were incubated with 20 pM $^{125}$I-GLP-1 in the presence of increasing concentrations of cold peptides. Each point was measured in duplicate and the experiments repeated three times for GLP-1, GIP and glucagon and once for VIP and secretin.

Figure 5:
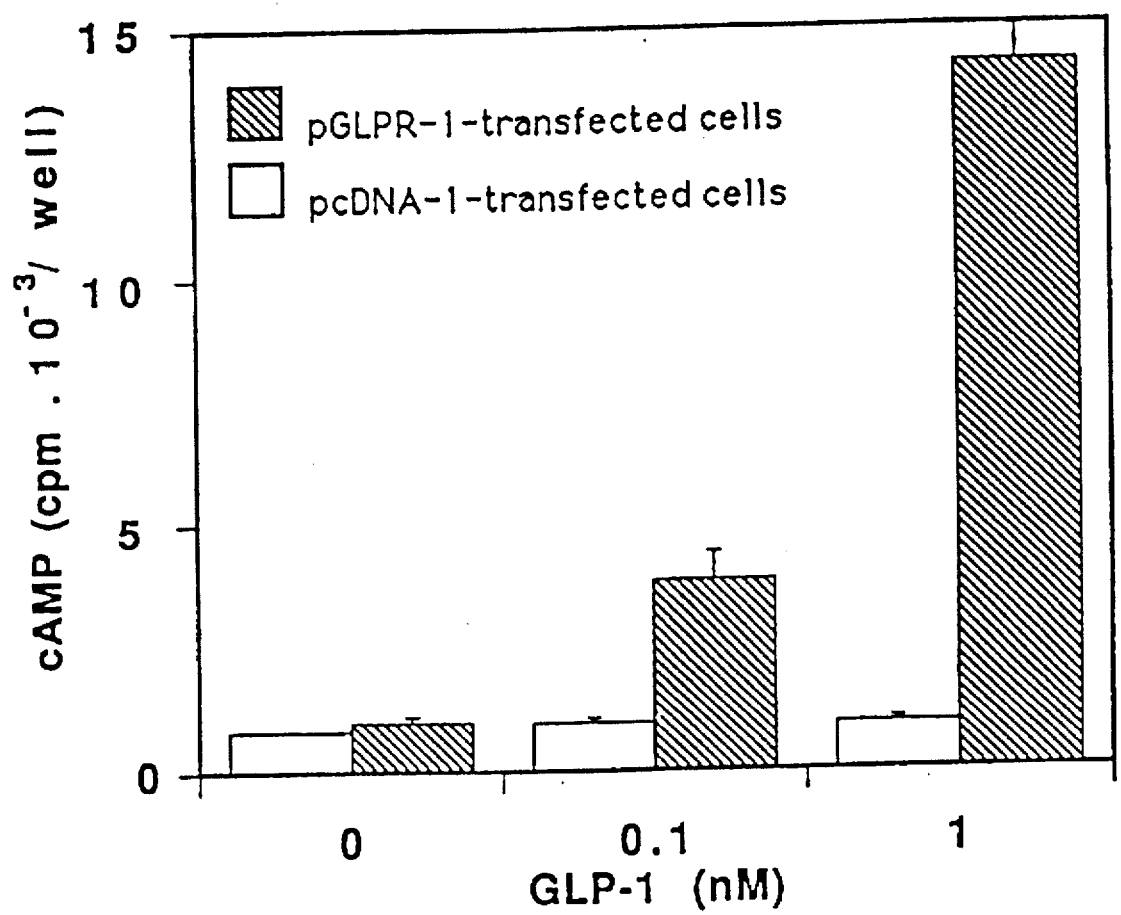

FIG. 5 shows stimulation of cyclic AMP formation in COS cells transfected with the rat GLP-1 receptor cDNA. COS cells were transfected with the pcDNA-1 vector alone (open bars) or the pGLPR-1 plasmid (stripped bar) and incubated in the absence or the presence of GLP-1 at the indicated concentration. cAMP production was measured in triplicate with a radioimmunoassay (Amersham).

Figure 6:
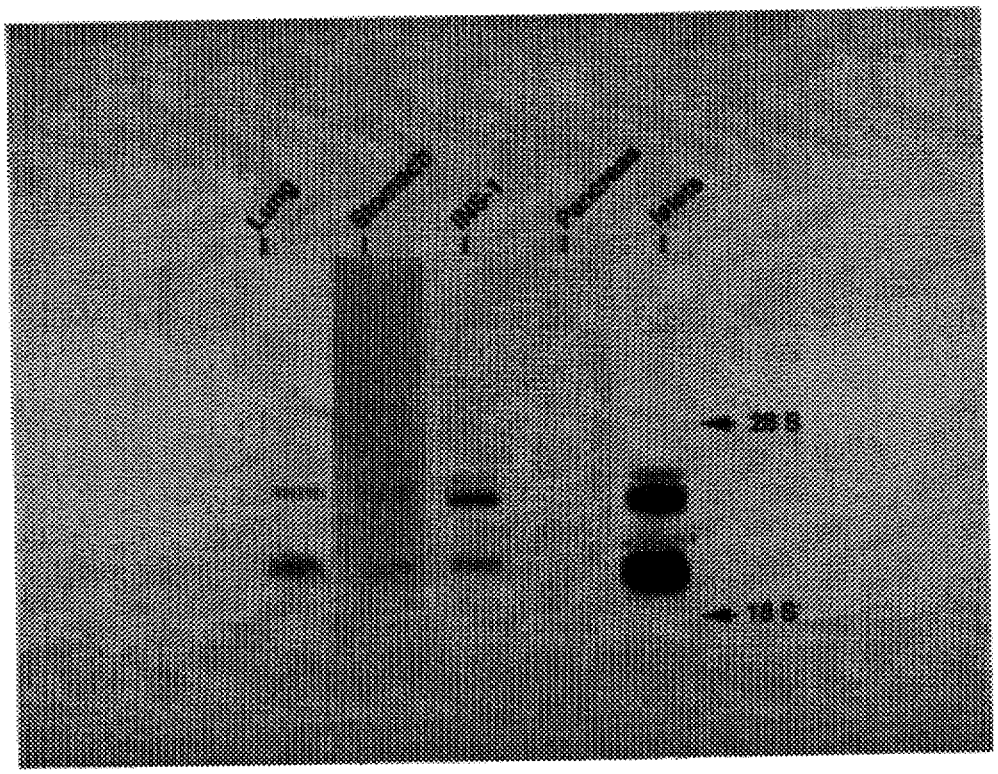

FIG. 6 shows tissue specificity of GLP-1 receptor expression assessed by Northern blotting of RNA from different tissues and from the INS-1 cell line. Ten micrograms of total RNA was analyzed on each lane. Two major RNA species of 2.7 and 3.6 kb were detected in all tissues in which the receptor was detected. The position of the migration of the ribosomal RNAs is indicated to the left of the picture.

FIG. 7 is a comparison of the rat GLP-1 receptor amino acid sequence (rat) and a partial amino acid sequence of the human GLP-1 receptor (human).

The present invention is further illustrated in the following examples which is not intended to be in any way limiting to the scope of the invention as claimed.

EXAMPLE 1

Molecular Cloning and Characterisation of the Rat Islet GLP-1 Receptor cDNA

A rat pancreatic islet cDNA library was constructed in the pcDNA-1 expression vector (Rat pancreatic islets were prepared according to Gotoh et al. (Transplantation 43 (1985), 725). PolyA+ RNA was prepared and the cDNA library was constructed in the pcDNA-1 vector (In Vitrogen) as described by Aruffo and Seed (Proc. Natl. Acad. Sci. USA 84 (1987), 8573) and Lin et al. (Proc. Natl. Acad. Sci. USA 88 (1991), 3185). Plasmid DNA was prepared from pools of five to eight thousands bacterial clones (Maniatis et al., Molecular Cloning. A Laboratory Manual. Cold Spring Harbor Laboratory, 1982) and transfected into COS cells (Sompayrac and Dana, Proc. Natl. Acad. Sci. USA 78 (1981), 7575). The presence of GLP-1 receptor expressed in COS cells was assessed by binding of the radioiodinated peptide followed by photographic emulsion autoradiography and screening by dark field microscopy (Gearing et al. EMBO J. 8 (1989), 3667). GLP-1(7-36)amide, as well as the other peptides, were purchased from Peninsula Laboratories. Iodination was performed by the iodine monochloride method (Contreras et al. Meth. Enzymol. 92 (1983), 277), the peptide was purified by passage over Sephadex G-10 followed by CM-Sepharose and specific activity was determined by the self displacement technique (Calvo et al. Biochem. 212 (1983), 259). A 1.6 kb cDNA clone (pGLPR-1) was isolated by subfractionation of an original positive pool and was used to isolate, by DNA hybridization screening, two additional clones from primary positive pools. These plasmids (pGLPR-16 and -87) had inserts of 3.0 and 2.0 kb, respectively. Transfection of these clones into COS cells generated high affinity ($K_D$=0.6 nM) binding sites for GLP-1 (FIG. 2). This affinity is comparable to that seen for binding of GLP-1 to the rat insulinoma cell line INS-1 (Asfari et al. Endocrinology 130 (1992), 167) ($K_D$= 0.12 nM; FIG. 3). In both cases a single high affinity binding component was detected. The binding to GLP-1 receptor transfected COS cells reached a plateau between 1 and 10 nM. At concentrations above 10 nM a second, high capacity, low affinity, binding component was detected. Although specifically displacable by cold GLP-1, this binding was also present in COS cells transfected with the expression vector alone and was therefore not further characterized.

Binding of GLP-1 to the receptor expressed in COS cells was displaced by cold GLP-1 with a 50 percent displacement achieved at 0.5 to 1 nM (FIG. 4). Other peptide hormones of related structure such as secretin, gastric inhibitory peptide (GIP) and vasoactive intestinal peptide (VIP) (Dupre in The Endocrine Pancreas, E. Samois Ed. (Raven Press, New York, (1991), 253–281) and Ebert and Creutzfeld, Diabetes Metab. Rev. 3, (1987) did not displace binding. Glucagon could displace the binding by 50 percent but only at a concentration of one micromolar (FIG. 4). The addition of subnanomolar concentrations of GLP-1 to transfected COS cells stimulated the production of cyclic AMP indicating that the receptor was functionally coupled to activation of adenylate cyclase (FIG. 5).

DNA sequence analysis of the rat GLP-1 receptor cDNA revealed a major open reading frame coding for a 463 amino acid polypeptide (SEQ ID No. 1). Hydrophaphy plot analysis indicated the presence of an amino-terminal hydrophobic region most probably representing a leader sequence. This hydrophobic segment is followed by a hydrophilic domain of about 120 amino acids which contains three N-linked glycosylation sites. Seven hydrophobic segments are present which may form transmembrane domains. Search for sequence identities showed the GLP-1 receptor to be homologous to the secretin receptor (Ishihara et al. EMBO J. 10 (1991), 1635) (40 percent identity), the parathyroid hormone receptor (Jüppner et al. (Science 254 (1991), 1024) (32.4 percent identity) and the calcitonin receptor (Lin et al. Science 254 (1991), 1022) (27.5 percent identity) (FIG. 1). These four receptors do not share any significant sequence homology with other known members of the G-coupled receptor family and are characterized by a relatively long amino terminal, probably extracellular, domain. The sequence of the extracellular domain is unique for each receptor, yet four cysteines are perfectly conserved (boxes in FIG. 1). A fifth cysteine at position 126 of the GLP-1 receptor is also conserved in the parathyroid and calcitonin receptors and at a similar location in the secretin receptor (position 123). The highest sequence identity between the four proteins resides in the transmembrane domains. The carboxyl terminal, cytoplasmic, ends of each receptor are also very different. These receptors all stimulate the production of cyclic AMP in response to ligand binding (Ishihara et al. EMBO J. 10 (1991), 1635), Jüpper et al. (Science 254 (1991), 1024) and Lin et al. Science 254 (1991), 1022) and are presumably coupled to the cyclase via Gsα. In that respect, it is interesting to note that a sequence motif present in the third cytoplasmic loop of the GLP-1 receptors (present just before the sixth transmembrane domain) is very similar to a motif of the beta2 adrenergic receptor present at the same location and whose basic amino acids have been shown to be important in the coupling of the receptor to Gsα (Okamoto et al. Cell 67 (1991), 723). Moreover, in the beta2 adrenergic receptor, this motif is preceded by a basic amino acid located twelve amino acid toward the amino-terminal end. This basic amino acid is also required at this particular distance for efficient coupling to Gsα. In the GLP-1 receptor a lysine residue is also present at a similar location. This suggests that, despite the very low overall sequence identity, a structural feature may have been conserved in the third cytoplasmic loop between the two receptors which, may be required for the coupling of receptor to the Gsα protein.

Determination of the tissue distribution of the GLP-1 receptor was performed by Northern blot analysis. Northern blot analysis was performed with 10 μg of total RNA (Chomczynski and Sacchi, Anal. Biochem. 126 (1987), 156) denatured with glyoxal (McMaster and Carmichael, Proc. Natl. Acad. Sci. USA 74 (1977), 4835) separated on a 1% agarose gel and transferred to Nylon membranes (Thomas, Proc. Natl. Acad. Sci. USA 77 (1980), 5201). Hybridization was performed with the random primed labelled (Feinberg and Vogelstein, Anal. Biochem. 132 (1983), 6) 1.6 kb pGLPR-1 insert. Two mRNAs of 2.7 and 3.6 kb could be detected in pancreatic islets as well as in rat insulinoma cell lines (INS-1), in stomach and in lung (FIG. 6). No GLP-1 receptor mRNA could be detected in brain, liver, thymus, muscle, intestine and colon. The presence of the GLP-1 receptor has been reported in stomach where the peptide inhibits acid secretion by parietal cells in in vivo experiments (Schjoldager et al. Dig. Dis. Sci. 34 (1989), 703) but stimulates acid secretion on isolated parietal glands (Schmidtler et al. Am. J. Physiol. 260 (1991), G940). Binding sites for GLP-1 have also ben reported in lung membrane preparations (Richter et al. FEBS Letter 1 (1990), 78) but the role of the hormone on lung physiology is not known.

A stable cell line expressing the cloned rat GLP-1 receptor was established by Ca-phosphate mediated transfection (Maniatis et al., Molecular Cloning. A Laboratory Manual. Cold Spring Harbor Laboratory, 1989) of the CHL cell line (ATCC CCL 39). The plasmid, pGLPR-1, which contains a 1.6 kb rat GLP-1 receptor cDNA insert cloned in the pCDNA-1 vector, was cotransfected with the pWL-neo plasmid (Stratagene, La Jolla, Calif.) into CHL cells. The pWL-neo plasmid contains the neomycin resistance gene. Stable clones were selected in medium containing 0.8 mg/ml G418. A stable transformant expressing an estimate of 70.000 rat GLP-1 receptors pr cell was selected by this scheme and further propagated in the presence of 80 μM G418. Membranes from this transformant was subsequently used in the high-volume-throughput-screening (HVTS) assay as described in Example 3. Characterization of the receptor expressed by the GLP-1 R/CHL cell line led to an estimated Kd of 0.8 nM for whole cells, 2.3 nM for cell membranes using $^{125}$I-GLP-1(7-36)amide as radioligand.

EXAMPLE 2

Molecular cloning of the human islet GLP-1 receptor cDNA

Human islets were prepared as described (Ricordi et al., Diabetes 37 (1988), 413–420), and poly-A$^+$ RNA was isolated by affinity chromatography by published methods (Gonda et al., Mol. Cell. Biol. 2 (1982) 617–624).

A human islet cDNA library was constructed in the λZAPII vector from Stratagene (La Jolla, Calif. ). Briefly, double stranded cDNA was synthesized as previously described (Aruffo and Seed, 84 (1987), 8573–8577; Thorens, Proc. Natl. Acad. Sci., USA 89 (1992), 8641–8645), and EcoRI/NotI adaptors (Stratagene, La Jolla, Calif.) were added with T$_4$ DNA ligase.

The resulting cDNA molecules were phosphorylated with T$_4$ polynucleotide kinase before size fractionation on potassium acetate gradients (Aruffo and Seed, 84. (1987), 8573–8577). Double stranded cDNA with a size above 1.6 kb was ligated into λZAPII arms (Stratagene, La Jolla, Calif. ), packaged in λ phage and grown on a lawn of XL-1 Blue E. coli cells as described in protocols from Stratagene.

The cDNA library was screened by hybridization to a $^{32}$P labelled DNA fragment from the rat GLP-1 receptor cDNA by previously described methods (Maniatis et al., Molecular Cloning. A Laboratory Manual. Cold Spring Harbour Laboratory, 1982). The reduced stringency conditions used were: prehybridization and hybridization in 30% formamide, 5× SSC, 5× Denhardt, 50 mM phosphate buffer pH 6.8, 5mM EDTA, 0.2% SDS and 100 μg/ml salmon sperm DNA at 42° C. Washings were 4×30 min in 2× SSC, 0.2% SDS at 42° C. (Maniatis et al., Molecular Cloning. A Laboratory Manual. Cold Spring Harbour Laboratory, 1982).

Positive λ phages were purified by replating and hybridization, the cDNA inserts contained in the Bluescript vector present in the λ ZAPII arms were excised using helper phages obtained from Stratagene (La Jolla, Calif.). The inserts were partially sequenced. One clone designated 3(20) showed high homology to the rat GLP-1 receptor and was sequenced (Tabor and Richardson, Proc. Natl. Acad. Sci., USA 84 (1987), 4767–4771) in its entire length. The DNA sequence is shown as SEQ ID No. 3.

From homology analysis (FIG. 7), it was concluded that this cDNA encoded the 3' part of the human GLP-1 receptor. The deduced amino acid sequence of the human receptor has 92% identity to the rat GLP-1 receptor in the region from amino acid number 170 to amino acid number 463 (numbers refer to the rat sequence).

The isolated human GLP-1 cDNA does not contain the entire open reading frame at the 5' end. However, a full length clone can easily be obtained by methods well known to persons skilled in the art. Among the alternative methods of choice, the following examples should be mentioned: 1) The human islet cDNA library can either be rescreened with a probe from the 5' end of the already cloned sequence. 2) Anchor-PCR or RACE (Rapid Amplification of cDNA Ends) (Kriangkum et al., Nucleic Acids Res. 20 (1992) 3793–3794; Troutt et al., Proc. Natl. Acad. Sci., USA 89 (1992), 9823–9825) methodology can be used to clone the remaining 5' sequences from islet RNA. 3) The remaining 5' part can be isolated from human genomic libraries, and DNA fragments considered to represent introns can be identified based on homology to the cDNA of the rat receptor and deleted by mutagenesis.

After cloning of the 5' end of the open reading frame, this part of the cDNA can be fused to the remaining 3' part of the human GLP-1 receptor cDNA by the use of PCR or through fusion at appropriate restriction enzyme recognition sequences identified in both the 5' and the 3' parts.

The cDNA encoding the full length open reading frame can be cloned in suitable mammalian expression vectors and transfected into mammalian cell lines for expression. Examples of such suitable cell lines are the CHO and CHL cells, but other mammalian cells will also express receptors of this type.

It has recently been demonstrated that insect cells (Vasudevan et al. FEBS Lett. 311 (1992), 7–11) and microorganisms like e.g. yeast (King et al., Science 250 (1990), 121–123) can express G-protein coupled receptors.

Recently frog skin melanophore cells have been used to express G-protein coupled receptors (Potenza et al, Analytical Biochem., 206, (1992), 315–322) and a functional coupling to adenylate cyclase was demonstrated.

Other microorganisms like Aspergillus, Bacillus, E. coli might be able to express these receptors after appropriate genetic engineering and selection.

It is therefore clear to persons skilled in the art that a number of different expression systems can be designed that will lead to expression of a functional receptor molecule. As demonstrated in Example 3, the rat as well as the human GLP-1 receptor can be used in screening assays for detection of new potential agonist lead structures.

EXAMPLE 3

High throughput screening assay for GLP-1 receptor agonists

Screening of microbial extracts for secondary metabolites with potential GLP-1 agonist activity was carried out using the SPA (Scintillation Proximity Assay) technology (U.S. Pat. No. 4,568,649, Hart and Greenwalt (Mol. Immunol., 16 (1979) 265–267), Udenfriend et al (Proc. Natl. Acad. Sci. USA, 82 (1985) 8672–8676). Wheatgerm agglutinin (WGA) coated SPA beads developed by Amersham International were used (U.S. Pat. NO 4,568,649, European patent 0154734, Japanese patent appl. 84/52452). The WGA coat allows GLP-1 receptor bearing membranes to be immobilized on the SPA beads. Membranes used in the screening assay were prepared from a CHL (ATTC CCL39) cell line expressing the cloned rat GLP-1 receptor as described in in Example 1. Membranes were prepared essentially as described by Unden et al (Eur. J. Biochem. 145 (1984), 525–530). The binding of $^{125}$I-GLP-1(7-36)amide to such immobilized receptors brings the tracer in close proximity to the scintillant present within the SPA beads resulting in the emission of light. Any unbound ligand will not generate a signal. Thus under assay conditions a microbial extract—containing a component capable of binding to the GLP-1 receptor and thereby displacing the tracer—may be identified by virtue of a reduction in signal intensity.

A high throughput assay was established using 96 well microtiter plates. The assay was optimized with regard to the amounts of WGA particles, membrane and tracer used. (The $^{125}$I-GLP-1(7-36)amide tracer was labelled using the lactoperoxidase method (Morrison et al., Methods Enzymol. 70 (1980), 214–219) followed by purification on reverse phase HPLC). Using a Packard TopCount™ microplate scintillation counter (Packard Instrument Company) these optimized conditions resulted in a $B_0$ of more than 7000 cpm. (Non specific binding determined in the presence of 500 nM unlabelled GLP-1(7-36)amide amounts to less than 1000 cpm. $IC_{50}$=0.5–1.0 nM GLP-1(7-36) amide).

So far 1250 microbial extracts have been screened using the SPA GLP-1 receptor assay. The extracts were tested at a final dilution of 1:400. Under these conditions 15 out of the 1250 extracts resulted in a reduction of specific counts to below the chosen cut-off level. These 15 hits have been further characterized in a secondary assay. This secondary assay was designed to test whether cAMP synthesis in a GLP-1 receptor bearing cell line can be induced by components in the extract. β-TC3 cells (Hanahan et al., Nature 315 (1985) 115–122) and Efrat et al (Proc. Natl. Acad. Sci. USA 85 (1988) 9037–9041) grown in 96-well microtiter plates were exposed to extracts diluted in culture media. After 20 min at 37° C. the cells were lysed by addition of acid and the cAMP concentration determined using the cyclic AMP SPA system (Amersham International). Of the 15 primary hits tested in this secondary assay, 5 extracts have been found to significantly increase the cAMP level in β-TC3 cells.

It has thus been demonstrated that it is feasible that the screening approach described in this patent application can result in the isolation of natural compounds with GLP-1 agonist activity. The use of such compounds as lead structures for a medicinal chemistry approach will be of significant importance in the design of novel GLP-1 agonists.

---

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 3066 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Rat ( i x ) FEATURE:
        ( A ) NAME/KEY: CDS
        ( B ) LOCATION: 17..1408

( x i ) SEQUENCE DESCRIPTION: SEQ ID NO:1:

```
TCCTGAGCGC  CCCGCC  ATG  GCC  GTC  ACC  CCC  AGC  CTG  CTG  CGC  CTG  GCG         49
                    Met  Ala  Val  Thr  Pro  Ser  Leu  Leu  Arg  Leu  Ala
                     1                   5                        10

CTC  CTG  CTG  CTC  GGG  GCG  GTG  GGC  AGG  GCC  GGC  CCC  CGC  CCC  CAG  GGT    97
Leu  Leu  Leu  Leu  Gly  Ala  Val  Gly  Arg  Ala  Gly  Pro  Arg  Pro  Gln  Gly
          15                        20                       25
```

-continued

| | | | | | | | | | | | | | | | | |
|---|---|---|---|---|---|---|---|---|---|---|---|---|---|---|---|---|
| GCC | ACG | GTG | TCC | CTC | TCA | GAG | ACA | GTG | CAG | AAA | TGG | AGA | GAG | TAT | CGG | 145 |
| Ala | Thr | Val | Ser | Leu | Ser | Glu | Thr | Val | Gln | Lys | Trp | Arg | Glu | Tyr | Arg | |
| | | 30 | | | | 35 | | | | | 40 | | | | | |
| CAC | CAG | TGC | CAA | CGT | TTC | CTC | ACG | GAA | GCG | CCA | CTC | CTG | GCC | ACA | GGT | 193 |
| His | Gln | Cys | Gln | Arg | Phe | Leu | Thr | Glu | Ala | Pro | Leu | Leu | Ala | Thr | Gly | |
| | | 45 | | | | 50 | | | | | 55 | | | | | |
| CTC | TTC | TGC | AAC | CGA | ACC | TTT | GAT | GAC | TAC | GCC | TGC | TGG | CCA | GAT | GGG | 241 |
| Leu | Phe | Cys | Asn | Arg | Thr | Phe | Asp | Asp | Tyr | Ala | Cys | Trp | Pro | Asp | Gly | |
| 60 | | | | | 65 | | | | 70 | | | | | | 75 | |
| CCC | CCA | GGT | TCC | TTT | GTG | AAT | GTC | AGT | TGC | CCC | TGG | TAC | CTG | CCG | TGG | 289 |
| Pro | Pro | Gly | Ser | Phe | Val | Asn | Val | Ser | Cys | Pro | Trp | Tyr | Leu | Pro | Trp | |
| | | | | 80 | | | | 85 | | | | | 90 | | | |
| GCC | AGT | AGT | GTG | CTC | CAA | GGG | CAT | GTG | TAC | CGG | TTC | TGC | ACG | GCC | GAG | 337 |
| Ala | Ser | Ser | Val | Leu | Gln | Gly | His | Val | Tyr | Arg | Phe | Cys | Thr | Ala | Glu | |
| | | | 95 | | | | 100 | | | | | 105 | | | | |
| GGT | ATC | TGG | CTG | CAT | AAG | GAC | AAC | TCC | AGC | CTG | CCC | TGG | AGG | GAC | CTG | 385 |
| Gly | Ile | Trp | Leu | His | Lys | Asp | Asn | Ser | Ser | Leu | Pro | Trp | Arg | Asp | Leu | |
| | | 110 | | | | | 115 | | | | | 120 | | | | |
| TCG | GAG | TGC | GAA | GAG | TCC | AAG | CAA | GGA | GAG | AGA | AAC | TCC | CCT | GAG | GAA | 433 |
| Ser | Glu | Cys | Glu | Glu | Ser | Lys | Gln | Gly | Glu | Arg | Asn | Ser | Pro | Glu | Glu | |
| | 125 | | | | | 130 | | | | | 135 | | | | | |
| CAG | CTC | CTG | TCG | CTG | TAC | ATT | ATC | TAC | ACG | GTG | GGG | TAC | GCA | CTT | TCT | 481 |
| Gln | Leu | Leu | Ser | Leu | Tyr | Ile | Ile | Tyr | Thr | Val | Gly | Tyr | Ala | Leu | Ser | |
| 140 | | | | | 145 | | | | | 150 | | | | | 155 | |
| TTC | TCT | GCC | TTG | GTC | ATC | GCT | TCA | GCC | ATC | CTT | GTC | AGC | TTC | AGA | CAC | 529 |
| Phe | Ser | Ala | Leu | Val | Ile | Ala | Ser | Ala | Ile | Leu | Val | Ser | Phe | Arg | His | |
| | | | | 160 | | | | | 165 | | | | | 170 | | |
| TTG | CAC | TGC | ACC | AGG | AAC | TAC | ATC | CAC | CTG | AAC | CTG | TTT | GCG | TCC | TTC | 577 |
| Leu | His | Cys | Thr | Arg | Asn | Tyr | Ile | His | Leu | Asn | Leu | Phe | Ala | Ser | Phe | |
| | | | 175 | | | | | 180 | | | | | 185 | | | |
| ATC | CTC | CGA | GCA | CTG | TCC | GTC | TTC | ATC | AAA | GAC | GCT | GCC | CTC | AAG | TGG | 625 |
| Ile | Leu | Arg | Ala | Leu | Ser | Val | Phe | Ile | Lys | Asp | Ala | Ala | Leu | Lys | Trp | |
| | | 190 | | | | | 195 | | | | | 200 | | | | |
| ATG | TAT | AGC | ACG | GCT | GCG | CAA | CAG | CAC | CAG | TGG | GAT | GGG | CTC | CTC | TCG | 673 |
| Met | Tyr | Ser | Thr | Ala | Ala | Gln | Gln | His | Gln | Trp | Asp | Gly | Leu | Leu | Ser | |
| | 205 | | | | | 210 | | | | | 215 | | | | | |
| TAT | CAG | GAC | TCT | CTG | GGC | TGC | CGA | CTG | GTG | TTC | CTG | CTC | ATG | CAA | TAC | 721 |
| Tyr | Gln | Asp | Ser | Leu | Gly | Cys | Arg | Leu | Val | Phe | Leu | Leu | Met | Gln | Tyr | |
| 220 | | | | | 225 | | | | | 230 | | | | | 235 | |
| TGC | GTG | GCG | GCC | AAC | TAC | TAC | TGG | TTG | CTG | GTG | GAA | GGC | GTG | TAT | CTG | 769 |
| Cys | Val | Ala | Ala | Asn | Tyr | Tyr | Trp | Leu | Leu | Val | Glu | Gly | Val | Tyr | Leu | |
| | | | | 240 | | | | | 245 | | | | | 250 | | |
| TAC | ACA | CTG | CTG | GCC | TTC | TCG | GTG | TTC | TCG | GAG | CAG | CGC | ATC | TTC | AAG | 817 |
| Tyr | Thr | Leu | Leu | Ala | Phe | Ser | Val | Phe | Ser | Glu | Gln | Arg | Ile | Phe | Lys | |
| | | | 255 | | | | | 260 | | | | | 265 | | | |
| CTG | TAC | CTG | AGC | ATA | GGC | TGG | GGA | GTT | CCG | CTG | CTG | TTC | GTT | ATC | CCC | 865 |
| Leu | Tyr | Leu | Ser | Ile | Gly | Trp | Gly | Val | Pro | Leu | Leu | Phe | Val | Ile | Pro | |
| | | 270 | | | | | 275 | | | | | 280 | | | | |
| TGG | GGC | ATT | GTC | AAG | TAT | CTC | TAC | GAG | GAC | GAG | GGT | TGC | TGG | ACC | AGG | 913 |
| Trp | Gly | Ile | Val | Lys | Tyr | Leu | Tyr | Glu | Asp | Glu | Gly | Cys | Trp | Thr | Arg | |
| | 285 | | | | | 290 | | | | | 295 | | | | | |
| AAC | TCC | AAC | ATG | AAC | TAT | TGG | CTC | ATC | ATA | CGC | TTG | CCC | ATT | CTC | TTT | 961 |
| Asn | Ser | Asn | Met | Asn | Tyr | Trp | Leu | Ile | Ile | Arg | Leu | Pro | Ile | Leu | Phe | |
| 300 | | | | | 305 | | | | | 310 | | | | | 315 | |
| GCA | ATC | GGG | GTC | AAC | TTC | CTT | GTC | TTC | ATC | CGG | GTC | ATC | TGC | ATC | GTG | 1009 |
| Ala | Ile | Gly | Val | Asn | Phe | Leu | Val | Phe | Ile | Arg | Val | Ile | Cys | Ile | Val | |
| | | | | 320 | | | | | 325 | | | | | 330 | | |
| ATA | GCC | AAG | CTG | AAG | GCT | AAT | CTC | ATG | TGT | AAG | ACC | GAC | ATC | AAA | TGC | 1057 |
| Ile | Ala | Lys | Leu | Lys | Ala | Asn | Leu | Met | Cys | Lys | Thr | Asp | Ile | Lys | Cys | |
| | | | 335 | | | | | 340 | | | | | 345 | | | |

-continued

| | | | | | | | | | | | | | | | |
|---|---|---|---|---|---|---|---|---|---|---|---|---|---|---|---|
| AGA | CTC | GCG | AAG | TCC | ACT | CTG | ACG | CTC | ATC | CCG | CTT | CTG | GGC | ACG | CAT |
| Arg | Leu | Ala | Lys | Ser | Thr | Leu | Thr | Leu | Ile | Pro | Leu | Leu | Gly | Thr | His |
| | | 350 | | | | 355 | | | | | | 360 | | | |

1105

| GAA | GTC | ATC | TTT | GCC | TTT | GTG | ATG | GAC | GAG | CAC | GCC | CGA | GGA | ACC | CTA |
|---|---|---|---|---|---|---|---|---|---|---|---|---|---|---|---|
| Glu | Val | Ile | Phe | Ala | Phe | Val | Met | Asp | Glu | His | Ala | Arg | Gly | Thr | Leu |
| | 365 | | | | | 370 | | | | | 375 | | | | |

1153

| CGC | TTC | GTC | AAG | CTG | TTC | ACA | GAG | CTC | TCC | TTC | ACT | TCC | TTC | CAG | GGC |
|---|---|---|---|---|---|---|---|---|---|---|---|---|---|---|---|
| Arg | Phe | Val | Lys | Leu | Phe | Thr | Glu | Leu | Ser | Phe | Thr | Ser | Phe | Gln | Gly |
| 380 | | | | | 385 | | | | | 390 | | | | | 395 |

1201

| TTT | ATG | GTG | GCT | GTC | TTG | TAC | TGC | TTT | GTC | AAC | AAT | GAG | GTC | CAG | ATG |
|---|---|---|---|---|---|---|---|---|---|---|---|---|---|---|---|
| Phe | Met | Val | Ala | Val | Leu | Tyr | Cys | Phe | Val | Asn | Asn | Glu | Val | Gln | Met |
| | | | | 400 | | | | | 405 | | | | | 410 | |

1249

| GAG | TTT | CGG | AAG | AGC | TGG | GAG | CGC | TGG | AGG | CTG | GAG | CGC | TTG | AAC | ATC |
|---|---|---|---|---|---|---|---|---|---|---|---|---|---|---|---|
| Glu | Phe | Arg | Lys | Ser | Trp | Glu | Arg | Trp | Arg | Leu | Glu | Arg | Leu | Asn | Ile |
| | | | 415 | | | | | 420 | | | | | 425 | | |

1297

| CAG | AGG | GAC | AGC | AGC | ATG | AAA | CCC | CTC | AAG | TGT | CCC | ACC | AGC | AGC | GTC |
|---|---|---|---|---|---|---|---|---|---|---|---|---|---|---|---|
| Gln | Arg | Asp | Ser | Ser | Met | Lys | Pro | Leu | Lys | Cys | Pro | Thr | Ser | Ser | Val |
| | | 430 | | | | | 435 | | | | | 440 | | | |

1345

| AGC | AGT | GGG | GCC | ACG | GTG | GGC | AGC | AGC | GTG | TAT | GCA | GCC | ACC | TGC | CAA |
|---|---|---|---|---|---|---|---|---|---|---|---|---|---|---|---|
| Ser | Ser | Gly | Ala | Thr | Val | Gly | Ser | Ser | Val | Tyr | Ala | Ala | Thr | Cys | Gln |
| | 445 | | | | | 450 | | | | | 455 | | | | |

1393

| AAT | TCC | TGC | AGC | TGAGCCCAG | TGCTGCGCTT | CCTGATGGTC | CTTGCTGCTG |
|---|---|---|---|---|---|---|---|
| Asn | Ser | Cys | Ser | | | | |
| 460 | | | | | | | |

1445

| | | | | |
|---|---|---|---|---|
| GCTGGGTGGC | CATCCCAGGT | GGGAGAGACC | CTGGGGACAG | GGAATATGAG | GGATACAGGC | 1505 |
| ACATGTGTGT | GCGTGCCCGC | ACACCACACA | CACACACACA | CACACACACA | CACACACACA | 1565 |
| CACACACACA | CACACGCTTT | CCTCCTCAAA | CCTATCAAAC | AGGCATCGGC | ATCGGCAGTG | 1625 |
| CCTCCTGGGA | CCACAGACAC | ATGTTCTCCA | AGGAGAACAG | CCTGCTAATT | TAATCTCAGG | 1685 |
| CGACAGGAAG | AGAGGAAGAA | ACAATTGCTG | TTAAGACGAG | GAGGACTTCT | TCCTGTTAAA | 1745 |
| GCTGCAAGGC | CCTTGGGGTT | CCCTCGGACA | GAACTGCAAA | TCAACCCCGG | AACTCTCGCT | 1805 |
| CAAGGGCAAT | TGCTGACGGG | TGGAACTTGG | GCTTGCGAGA | GGAGGCAGGT | CCATGAGAGA | 1865 |
| CCTGCCCTTG | GAACCTCAGC | CAGCACAGCG | CTCATCAAGG | TGAGCTGGCT | GTGCTGTGTG | 1925 |
| CACGGCTGGG | GTTGTCACCT | ACATCAGCCT | TCCTCTCGGA | CAAGAGGCTT | TTCTCTGTGC | 1985 |
| ATCTGGAGTG | CCGCCATTCC | TCCATCTGCC | CGTTCATCCG | CCATCCTGTC | TTTGCCTTGG | 2045 |
| GGAGGGGGAG | GTTTGTTGAA | GTCATGCCGT | GCAGCTCTTT | CTGGAAATAT | CTGTGGATGG | 2105 |
| TGTTGAAGAT | AAGCATGGGG | GAGATACAAC | AGAGGCAGTC | TTTGCCCATG | GCCACTTCTT | 2165 |
| GCCTGGTCCT | TTAAGCCACT | TTGCTGCTTG | GTTTCTGCCC | TGCATGGGTA | CTACTAGGGC | 2225 |
| AGGTCCCAAG | TTGAGAAGCC | CAGAGGTGAG | GTGTGAACCC | TCAGTTCTGT | TGTAAAGATG | 2285 |
| CTCAAATACC | CTCTAAGGTT | CATCTAAAGG | AGTAACCTGC | CTAGGGGTGC | TGTTGACCTG | 2345 |
| AAATCAAGAG | GACCAAAGGA | TCCATTGCCA | ACACCCCCCA | TCCCCACAC | ACACCTCATC | 2405 |
| TGTGACCAGA | GTCTATGCTT | TGAATCAGAA | TGGGCTATAT | CCTCTGACCT | CAGAGGCTAT | 2465 |
| GACCCAGAAG | AGATTCTTCC | CTGAATCCTC | CCACTTTGCA | CACATATAGA | CTTTATCCTT | 2525 |
| CTTCACTCTG | TGTCTATTCA | AACGTATAAT | TCTGGTTTCT | CTCACCCCAC | GGAAGAACTA | 2585 |
| GATCACAGCA | ACTGTTATGT | TTGAGGGAGT | GGGGGAGAAG | GTGATTGATT | TGACCCCCTC | 2645 |
| TCCCCCACCG | GTGTTGATAA | GTAGCGTCTG | TCCCACCTCC | AGACTCCACC | CACACATAAT | 2705 |
| GAGCAGCACA | TAGACCAGGA | TGGGGGGGGT | GGTATATCAT | GCTTGCCCTC | CTCCAACCAC | 2765 |
| TATGAGAAGG | CTAGCAGAAG | ACACCACTGC | ACAGACCCAA | GTCCAAGGAC | TGCCTCCCAG | 2825 |
| GGAATTAGGC | AGTGACTTCC | TAGAGGCCAA | GAAAGACTCC | AAGAGCTGGA | GAAGAATCCT | 2885 |

```
AGTCGATCTG GATCTCTTTT GAGGTTGGGG TTGGGGTGGC TTTCAATGGA TTCTCTCATG      2945

AGGCTTATCT CTCCCTCATC CCGTGGAGAG TGGGGGACCC TCCCTAGTGC TCACACTAGA      3005

CACTGTGCCC CTTGGAGAGG CATAAGGCAT GTATGGGAGA TAATAATGGG CTATAAAACA      3065

T                                                                      3066
```

( 2 ) INFORMATION FOR SEQ ID NO:2:

( i ) SEQUENCE CHARACTERISTICS:
        ( A ) LENGTH: 463 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Val Thr Pro Ser Leu Leu Arg Leu Ala Leu Leu Leu Leu Gly
 1               5                  10                  15

Ala Val Gly Arg Ala Gly Pro Arg Pro Gln Gly Ala Thr Val Ser Leu
            20                  25                  30

Ser Glu Thr Val Gln Lys Trp Arg Glu Tyr Arg His Gln Cys Gln Arg
        35                  40                  45

Phe Leu Thr Glu Ala Pro Leu Leu Ala Thr Gly Leu Phe Cys Asn Arg
 50                  55                  60

Thr Phe Asp Asp Tyr Ala Cys Trp Pro Asp Gly Pro Pro Gly Ser Phe
 65                  70                  75                  80

Val Asn Val Ser Cys Pro Trp Tyr Leu Pro Trp Ala Ser Ser Val Leu
                 85                  90                  95

Gln Gly His Val Tyr Arg Phe Cys Thr Ala Glu Gly Ile Trp Leu His
            100                 105                 110

Lys Asp Asn Ser Ser Leu Pro Trp Arg Asp Leu Ser Glu Cys Glu Glu
        115                 120                 125

Ser Lys Gln Gly Glu Arg Asn Ser Pro Glu Glu Gln Leu Leu Ser Leu
    130                 135                 140

Tyr Ile Ile Tyr Thr Val Gly Tyr Ala Leu Ser Phe Ser Ala Leu Val
145                 150                 155                 160

Ile Ala Ser Ala Ile Leu Val Ser Phe Arg His Leu His Cys Thr Arg
                165                 170                 175

Asn Tyr Ile His Leu Asn Leu Phe Ala Ser Phe Ile Leu Arg Ala Leu
            180                 185                 190

Ser Val Phe Ile Lys Asp Ala Ala Leu Lys Trp Met Tyr Ser Thr Ala
        195                 200                 205

Ala Gln Gln His Gln Trp Asp Gly Leu Leu Ser Tyr Gln Asp Ser Leu
    210                 215                 220

Gly Cys Arg Leu Val Phe Leu Leu Met Gln Tyr Cys Val Ala Ala Asn
225                 230                 235                 240

Tyr Tyr Trp Leu Leu Val Glu Gly Val Tyr Leu Tyr Thr Leu Leu Ala
                245                 250                 255

Phe Ser Val Phe Ser Glu Gln Arg Ile Phe Lys Leu Tyr Leu Ser Ile
            260                 265                 270

Gly Trp Gly Val Pro Leu Leu Phe Val Ile Pro Trp Gly Ile Val Lys
        275                 280                 285

Tyr Leu Tyr Glu Asp Glu Gly Cys Trp Thr Arg Asn Ser Asn Met Asn
    290                 295                 300

Tyr Trp Leu Ile Ile Arg Leu Pro Ile Leu Phe Ala Ile Gly Val Asn
305                 310                 315                 320
```

-continued

| | | | | | | | | | | | | | | |
|---|---|---|---|---|---|---|---|---|---|---|---|---|---|---|
|Phe|Leu|Val|Phe|Ile<br>325|Arg|Val|Ile|Cys<br>330|Val|Ile|Ala|Lys|Leu<br>335|Lys|
|Ala|Asn|Leu|Met<br>340|Cys|Lys|Thr|Asp|Ile<br>345|Lys|Cys|Arg|Leu|Ala<br>350|Lys|Ser|
|Thr|Leu|Thr<br>355|Leu|Ile|Pro|Leu|Leu<br>360|Gly|Thr|His|Glu|Val<br>365|Ile|Phe|Ala|
|Phe|Val<br>370|Met|Asp|Glu|His|Ala<br>375|Arg|Gly|Thr|Leu|Arg<br>380|Phe|Val|Lys|Leu|
|Phe<br>385|Thr|Glu|Leu|Ser|Phe<br>390|Thr|Ser|Phe|Gln|Gly<br>395|Phe|Met|Val|Ala|Val<br>400|
|Leu|Tyr|Cys|Phe|Val<br>405|Asn|Asn|Glu|Val|Gln<br>410|Met|Glu|Phe|Arg|Lys<br>415|Ser|
|Trp|Glu|Arg|Trp<br>420|Arg|Leu|Glu|Arg|Leu<br>425|Asn|Ile|Gln|Arg|Asp<br>430|Ser|Ser|
|Met|Lys|Pro<br>435|Leu|Lys|Cys|Pro|Thr<br>440|Ser|Ser|Val|Ser|Ser<br>445|Gly|Ala|Thr|
|Val|Gly<br>450|Ser|Ser|Val|Tyr|Ala<br>455|Ala|Thr|Cys|Gln|Asn<br>460|Ser|Cys|Ser|

( 2 ) INFORMATION FOR SEQ ID NO:3:

( i ) SEQUENCE CHARACTERISTICS:
        ( A ) LENGTH: 1909 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( i x ) FEATURE:
        ( A ) NAME/KEY: CDS
        ( B ) LOCATION: 3..887

( x i ) SEQUENCE DESCRIPTION: SEQ ID NO:3:

| | | | | | | | | | | | | | | | | |
|---|---|---|---|---|---|---|---|---|---|---|---|---|---|---|---|---|
|TC|AGA<br>Arg<br>1|CAC<br>His|CTG<br>Leu|TAC<br>Tyr|TGC<br>Cys<br>5|ACC<br>Thr|AGG<br>Arg|AAC<br>Asn|TAC<br>Tyr|ATC<br>Ile<br>10|CAC<br>His|CTG<br>Leu|AAC<br>Asn|CTG<br>Leu|TTT<br>Phe<br>15|47|
|GCA<br>Ala|TCC<br>Ser|TTC<br>Phe|ATC<br>Ile|CTG<br>Leu<br>20|CGA<br>Arg|GCA<br>Ala|TTG<br>Leu|TCC<br>Ser|GTC<br>Val<br>25|TTC<br>Phe|ATC<br>Ile|AAG<br>Lys|GAC<br>Asp|GCA<br>Ala<br>30|GCC<br>Ala|95|
|CTG<br>Leu|AAG<br>Lys|TGG<br>Trp|ATG<br>Met<br>35|TAT<br>Tyr|AGC<br>Ser|ACA<br>Thr|GCC<br>Ala|GCC<br>Ala<br>40|CAG<br>Gln|CAG<br>Gln|CAC<br>His|CAG<br>Gln|TGG<br>Trp<br>45|GAT<br>Asp|GGG<br>Gly|143|
|CTC<br>Leu|CTC<br>Leu|TCC<br>Ser<br>50|TAC<br>Tyr|CAG<br>Gln|GAC<br>Asp|TCT<br>Ser|CTG<br>Leu<br>55|AGC<br>Ser|TGC<br>Cys|CGC<br>Arg|CTG<br>Leu|GTG<br>Val<br>60|TTT<br>Phe|CTG<br>Leu|CTC<br>Leu|191|
|ATG<br>Met|CAG<br>Gln<br>65|TAC<br>Tyr|TGT<br>Cys|GTG<br>Val|GCG<br>Ala|GCC<br>Ala<br>70|AAT<br>Asn|TAC<br>Tyr|TAC<br>Tyr|TGG<br>Trp|CTC<br>Leu<br>75|TTG<br>Leu|GTG<br>Val|GAG<br>Glu|GGC<br>Gly|239|
|GTG<br>Val<br>80|TAC<br>Tyr|CTG<br>Leu|TAC<br>Tyr|ACA<br>Thr|CTG<br>Leu<br>85|CTG<br>Leu|GCC<br>Ala|TTC<br>Phe|TCG<br>Ser|GTG<br>Val<br>90|TTC<br>Phe|TCT<br>Ser|GAG<br>Glu|CAA<br>Gln|TGG<br>Trp<br>95|287|
|ATC<br>Ile|TTC<br>Phe|AGG<br>Arg|CTC<br>Leu|TAC<br>Tyr<br>100|GTG<br>Val|AGC<br>Ser|ATA<br>Ile|GGC<br>Gly|TGG<br>Trp<br>105|GGT<br>Gly|GTT<br>Val|CCC<br>Pro|CTG<br>Leu|CTG<br>Leu<br>110|TTT<br>Phe|335|
|GTT<br>Val|GTC<br>Val|CCC<br>Pro|TGG<br>Trp<br>115|GGC<br>Gly|ATT<br>Ile|GTC<br>Val|AAG<br>Lys|ATC<br>Ile<br>120|CTC<br>Leu|TAT<br>Tyr|GAG<br>Glu|GAC<br>Asp|GAG<br>Glu<br>125|GGC<br>Gly|TGC<br>Cys|383|

```
TGG ACC AGG AAC TCC AAC ATG AAC TAC TGG CTC ATT ATC CGG CTG CCC         431
Trp Thr Arg Asn Ser Asn Met Asn Tyr Trp Leu Ile Ile Arg Leu Pro
        130                 135                 140

ATT CTC TTT GCC ATT GGG GTG AAC TTC CTC ATC TTT GTT CGG GTC ATC         479
Ile Leu Phe Ala Ile Gly Val Asn Phe Leu Ile Phe Val Arg Val Ile
    145                 150                 155

TGC ATC GTG GTA TCC AAA CTG AAG GCC AAT GTC ATG TGC AAG ACA GAC         527
Cys Ile Val Val Ser Lys Leu Lys Ala Asn Val Met Cys Lys Thr Asp
160                 165                 170                 175

ATC AAA TGC AGA CTT GCC AAG TCC ACG CTG ACA CTC ATC CCC CTG CTG         575
Ile Lys Cys Arg Leu Ala Lys Ser Thr Leu Thr Leu Ile Pro Leu Leu
                180                 185                 190

GGG ACT CAT GAG GTC ATC TTT GCC TTT GTG ATG GAC GAG CAC GCC CGG         623
Gly Thr His Glu Val Ile Phe Ala Phe Val Met Asp Glu His Ala Arg
            195                 200                 205

GGG ACC CTG CGC TTC ATC AAG CTG TTT ACA GAG CTC TCC TTC ACC TCC         671
Gly Thr Leu Arg Phe Ile Lys Leu Phe Thr Glu Leu Ser Phe Thr Ser
        210                 215                 220

TTC CAG GGG CTG ATG GTG GCC ATC TTA TAC TGC TTT GTC AAC AAT GAG         719
Phe Gln Gly Leu Met Val Ala Ile Leu Tyr Cys Phe Val Asn Asn Glu
    225                 230                 235

GTC CAG CTG GAA TTT CGG AAG AGC TGG GAG CGC TGG CGG CTT GAG CAC         767
Val Gln Leu Glu Phe Arg Lys Ser Trp Glu Arg Trp Arg Leu Glu His
240                 245                 250                 255

TTG CAC ATC CAG AGG GAC AGC AGC ATG AAG CCC CTC AAG TGT CCC ACC         815
Leu His Ile Gln Arg Asp Ser Ser Met Lys Pro Leu Lys Cys Pro Thr
                260                 265                 270

AGC AGC CTG AGC AGT GGA GCC ACG GCG GGC AGC AGC ATG TAC ACA GCC         863
Ser Ser Leu Ser Ser Gly Ala Thr Ala Gly Ser Ser Met Tyr Thr Ala
            275                 280                 285

ACT TGC CAG GCC TCC TGC AGC TGAGACTCCA GCGCCTGCCC TCCCTGGGGT            914
Thr Cys Gln Ala Ser Cys Ser
        290                 295

CCTTGCTGCG GCCGGGTGGC AATCCAGGAG AAGCAGCCTC CTAATTTGAT CACAGTGGCG       974

AGAGGAGAGG AAAAACGATC GCTGTGAAAA TGAGGAGGAT TGCTTCTTGT GAAACCACAG      1034

GCCCTTGGGG TTCCCCCAGA CAGAGCCGCA AATCAACCCC AGACTCAAAC TCAAGGTCAA      1094

CGGCTTATTA GTGAAACTGG GGCTTGCAAG AGGAGGTGGT TCTGAAAGTG GCTCTTCTAA      1154

CCTCAGCCAA ACACGAGCGG GAGTGACGGG AGCCTCCTCT GCTTGCATCA CTTGGGGTCA      1214

CCACCCTCCC CTGTCTTCTC TCAAAGGGAA GCTGTTTGTG TGTCTGGGTT GCTTATTTCC      1274

CTCATCTTGC CCCCTCATCT CACTGCCCAG TTTCTTTTTG AGGGCTTGTT GGCCACTGCC      1334

AGCAGCTGTT TCTGGAAATG GCTGTAGGTG GTGTTGAGAA AGAATGAGCA TTGAGACACG      1394

GTGCTCGCTT CTCCTCCAGG TATTTGAGTT GTTTTGGTGC CTGCCTCTGC CATGCCCAGA      1454

GAATCAGGGC AGGCTTGCCA CCGGGGAACC CAGCCCTGGG GTATGAGCTG CCAAGTCTAT      1514

TTTAAAGACG CTCAAGAATC CTCTGGGGTT CATCTAGGGA CACGTTAGGA ATGTCCAGAC      1574

TGTGGGTGTA GGTTACCTGC CACTTCCAGG ACGCAGAGGG CCAAGAGAGA CATTGCCTCC      1634

ACCTCTCCTG AATACTTATC TGTGACCACA CGCTGTCTCT TGAGATTTGG ATACACTCTC      1694

TAGCTTTAGG GGACCATGAA GAGACTCTCT TAGGAAACCA ATAGTCCCCA TCAGCACCAT      1754

GGAGGCAGGC TCCCCCTGCC TTTGAAATTC CCCCACTTGG GAGCTGATAT ACTTCACTCA      1814

CTTTTCTTTA TTGCTGTGAT AGTCTGTGTG CACAATGGGC AATTCTGACT TCTCCCATCT      1874

AGTGAAATGA GCGAAATCAT GGTTGTAGTG ATCTT                                 1909
```

(2) INFORMATION FOR SEQ ID NO:4:

(i) SEQUENCE CHARACTERISTICS:
        (A) LENGTH: 294 amino acids
        (B) TYPE: amino acid
        (D) TOPOLOGY: linear (ii) MOLECULE TYPE: protein (xi) SEQUENCE DESCRIPTION: SEQ ID NO:4:

```
Arg His Leu Tyr Cys Thr Arg Asn Tyr Ile His Leu Asn Leu Phe Ala
 1               5                  10                  15
Ser Phe Ile Leu Arg Ala Leu Ser Val Phe Ile Lys Asp Ala Ala Leu
            20                  25                  30
Lys Trp Met Tyr Ser Thr Ala Ala Gln Gln His Gln Trp Asp Gly Leu
        35                  40                  45
Leu Ser Tyr Gln Asp Ser Leu Ser Cys Arg Leu Val Phe Leu Leu Met
    50                  55                  60
Gln Tyr Cys Val Ala Ala Asn Tyr Tyr Trp Leu Leu Val Glu Gly Val
65                  70                  75                  80
Tyr Leu Tyr Thr Leu Leu Ala Phe Ser Val Phe Ser Glu Gln Trp Ile
                85                  90                  95
Phe Arg Leu Tyr Val Ser Ile Gly Trp Gly Val Pro Leu Leu Phe Val
            100                 105                 110
Val Pro Trp Gly Ile Val Lys Ile Leu Tyr Glu Asp Glu Gly Cys Trp
        115                 120                 125
Thr Arg Asn Ser Asn Met Asn Tyr Trp Leu Ile Ile Arg Leu Pro Ile
    130                 135                 140
Leu Phe Ala Ile Gly Val Asn Phe Leu Ile Phe Val Arg Val Ile Cys
145                 150                 155                 160
Ile Val Val Ser Lys Leu Lys Ala Asn Val Met Cys Lys Thr Asp Ile
                165                 170                 175
Lys Cys Arg Leu Ala Lys Ser Thr Leu Thr Leu Ile Pro Leu Leu Gly
            180                 185                 190
Thr His Glu Val Ile Phe Ala Phe Val Met Asp Glu His Ala Arg Gly
        195                 200                 205
Thr Leu Arg Phe Ile Lys Leu Phe Thr Glu Leu Ser Phe Thr Ser Phe
    210                 215                 220
Gln Gly Leu Met Val Ala Ile Leu Tyr Cys Phe Val Asn Asn Glu Val
225                 230                 235                 240
Gln Leu Glu Phe Arg Lys Ser Trp Glu Arg Trp Arg Leu Glu His Leu
                245                 250                 255
His Ile Gln Arg Asp Ser Ser Met Lys Pro Leu Lys Cys Pro Thr Ser
            260                 265                 270
Ser Leu Ser Ser Gly Ala Thr Ala Gly Ser Ser Met Tyr Thr Ala Thr
    275                 280                 285
Cys Gln Ala Ser Cys Ser
290
```

(2) INFORMATION FOR SEQ ID NO: 5:

(i) SEQUENCE CHARACTERISTICS:
        (A) LENGTH: 449 amino acids
        (B) TYPE: amino acid
        (C) STRANDEDNESS: single
        (D) TOPOLOGY: linear (ii) MOLECULE TYPE: protein (iii) HYPOTHETICAL: NO ( i i i ) ANTI-SENSE: NO ( v i ) ORIGINAL SOURCE:
    ( A ) ORGANISM: Rattus norvegicus
    ( B ) STRAIN: Sprague-Dawley ( x i ) SEQUENCE DESCRIPTION: SEQ ID NO: 5:

```
Met Leu Ser Thr Met Arg Pro Arg Leu Ser Leu Leu Leu Arg Leu
 1               5                  10                  15

Leu Leu Leu Thr Lys Ala Ala His Thr Val Gly Val Pro Arg Leu
             20                  25                  30

Cys Asp Val Arg Arg Val Leu Leu Glu Glu Arg Ala His Cys Leu Gln
         35                  40                  45

Gln Leu Ser Lys Glu Lys Lys Gly Ala Leu Gly Pro Glu Thr Ala Ser
     50                  55                  60

Gly Cys Glu Gly Leu Trp Asp Asn Met Ser Cys Trp Pro Ser Ser Ala
 65                  70                  75                  80

Pro Ala Arg Thr Val Glu Val Gln Cys Pro Lys Phe Leu Leu Met Leu
             85                  90                  95

Ser Asn Lys Asn Gly Ser Leu Phe Arg Asn Cys Thr Gln Asp Gly Trp
             100                 105                 110

Ser Glu Thr Phe Pro Arg Pro Asp Leu Ala Cys Gly Val Asn Ile Asn
         115                 120                 125

Asn Ser Phe Asn Glu Arg Arg His Ala Tyr Leu Leu Lys Leu Lys Val
    130                 135                 140

Met Tyr Thr Val Gly Tyr Ser Ser Ser Leu Ala Met Leu Leu Val Ala
145                 150                 155                 160

Leu Ser Ile Leu Cys Ser Phe Arg Arg Leu His Cys Thr Arg Asn Tyr
                 165                 170                 175

Ile His Met His Leu Phe Val Ser Phe Ile Leu Arg Ala Leu Ser Asn
             180                 185                 190

Phe Ile Lys Asp Ala Val Leu Phe Ser Ser Asp Asp Val Thr Tyr Cys
         195                 200                 205

Asp Ala His Lys Val Gly Cys Lys Leu Val Met Ile Phe Phe Gln Tyr
    210                 215                 220

Cys Ile Met Ala Asn Tyr Ala Trp Leu Leu Val Glu Gly Leu Tyr Leu
225                 230                 235                 240

His Thr Leu Leu Ala Ile Ser Phe Phe Ser Glu Arg Lys Tyr Leu Gln
             245                 250                 255

Ala Phe Val Leu Leu Gly Trp Gly Ser Pro Ala Ile Phe Val Ala Leu
         260                 265                 270

Trp Ala Ile Thr Arg His Phe Leu Glu Asn Thr Gly Cys Trp Asp Ile
         275                 280                 285

Asn Ala Asn Ala Ser Val Trp Trp Val Ile Arg Gly Pro Val Ile Leu
    290                 295                 300

Ser Ile Leu Ile Asn Phe Ile Phe Phe Ile Asn Ile Leu Arg Ile Leu
305                 310                 315                 320

Met Arg Lys Leu Arg Thr Gln Glu Thr Arg Gly Ser Glu Thr Asn His
                 325                 330                 335

Tyr Lys Arg Leu Ala Lys Ser Thr Leu Leu Leu Ile Pro Leu Phe Gly
         340                 345                 350

Ile His Tyr Ile Val Phe Ala Phe Ser Pro Glu Asp Ala Met Glu Val
    355                 360                 365

Gln Leu Phe Phe Glu Leu Ala Leu Gly Ser Phe Gln Gly Leu Val Val
    370                 375                 380
```

| | | | | | | | | | | | | | | | |
|---|---|---|---|---|---|---|---|---|---|---|---|---|---|---|---|
| Ala | Val | Leu | Tyr | Cys | Phe | Leu | Asn | Gly | Glu | Val | Gln | Leu | Glu | Val | Gln |
| 385 | | | | | 390 | | | | 395 | | | | | | 400 |
| Lys | Lys | Trp | Arg | Gln | Trp | His | Leu | Gln | Glu | Phe | Pro | Leu | Arg | Pro | Val |
| | | | | 405 | | | | | 410 | | | | | 415 | |
| Ala | Phe | Asn | Asn | Ser | Phe | Ser | Asn | Ala | Thr | Asn | Gly | Pro | Thr | His | Ser |
| | | | 420 | | | | | 425 | | | | | 430 | | |
| Thr | Lys | Ala | Ser | Thr | Glu | Gln | Ser | Arg | Ser | Ile | Pro | Arg | Ala | Ser | Ile |
| | | 435 | | | | 440 | | | | | | 445 | | | |
| Ile | | | | | | | | | | | | | | | |

( 2 ) INFORMATION FOR SEQ ID NO: 6:

( i ) SEQUENCE CHARACTERISTICS:
        ( A ) LENGTH: 585 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i i i ) ANTI-SENSE: NO ( v i ) ORIGINAL SOURCE:
        ( A ) ORGANISM: Didelphis virginiana ( x i ) SEQUENCE DESCRIPTION: SEQ ID NO: 6:

| | | | | | | | | | | | | | | | |
|---|---|---|---|---|---|---|---|---|---|---|---|---|---|---|---|
| Met | Gly | Ala | Pro | Arg | Ile | Ser | His | Ser | Leu | Ala | Leu | Leu | Leu | Cys | Cys |
| 1 | | | | 5 | | | | | 10 | | | | | 15 | |
| Ser | Val | Leu | Ser | Ser | Val | Tyr | Ala | Leu | Val | Asp | Ala | Asp | Val | Ile | |
| | | | 20 | | | | 25 | | | | | 30 | | | |
| Thr | Lys | Glu | Glu | Gln | Ile | Ile | Leu | Leu | Arg | Asn | Ala | Gln | Ala | Gln | Cys |
| | | 35 | | | | | 40 | | | | | 45 | | | |
| Glu | Gln | Arg | Leu | Lys | Glu | Val | Leu | Arg | Val | Pro | Glu | Leu | Ala | Glu | Ser |
| | 50 | | | | | 55 | | | | | 60 | | | | |
| Ala | Lys | Asp | Trp | Met | Ser | Arg | Ser | Ala | Lys | Thr | Lys | Lys | Glu | Lys | Pro |
| 65 | | | | | 70 | | | | | 75 | | | | | 80 |
| Ala | Glu | Lys | Leu | Tyr | Ser | Gln | Ala | Glu | Glu | Ser | Arg | Glu | Val | Ser | Asp |
| | | | | 85 | | | | | 90 | | | | | 95 | |
| Arg | Ser | Arg | Leu | Gln | Asp | Gly | Phe | Cys | Leu | Pro | Glu | Trp | Asp | Asn | Ile |
| | | | | 100 | | | | | 105 | | | | | 110 | |
| Val | Cys | Trp | Pro | Ala | Gly | Val | Pro | Gly | Lys | Val | Val | Ala | Val | Pro | Cys |
| | | | 115 | | | | | 120 | | | | | 125 | | |
| Pro | Asp | Tyr | Ile | Tyr | Asp | Phe | Asn | His | Lys | Gly | Arg | Ala | Tyr | Arg | Arg |
| | | 130 | | | | | 135 | | | | | 140 | | | |
| Cys | Asp | Ser | Asn | Gly | Ser | Trp | Glu | Leu | Val | Pro | Gly | Asn | Asn | Arg | Thr |
| 145 | | | | | 150 | | | | | 155 | | | | | 160 |
| Trp | Ala | Asn | Tyr | Ser | Glu | Cys | Val | Lys | Phe | Leu | Thr | Asn | Glu | Thr | Arg |
| | | | | 165 | | | | | 170 | | | | | 175 | |
| Glu | Arg | Glu | Val | Phe | Asp | Arg | Leu | Gly | Met | Ile | Tyr | Thr | Val | Gly | Tyr |
| | | | 180 | | | | | 185 | | | | | 190 | | |
| Ser | Ile | Ser | Leu | Gly | Ser | Leu | Thr | Val | Ala | Val | Leu | Ile | Leu | Gly | Tyr |
| | | 195 | | | | | 200 | | | | | 205 | | | |
| Phe | Arg | Arg | Leu | His | Cys | Thr | Arg | Asn | Tyr | Ile | His | Met | His | Leu | Phe |
| | 210 | | | | | 215 | | | | | 220 | | | | |
| Val | Ser | Phe | Met | Leu | Arg | Ala | Val | Ser | Ile | Phe | Ile | Lys | Asp | Ala | Val |
| 225 | | | | | 230 | | | | | 235 | | | | | 240 |

```
Leu Tyr Ser Gly Val Ser Thr Asp Glu Ile Glu Arg Ile Thr Glu Glu
                245                 250                 255

Glu Leu Arg Ala Phe Thr Glu Pro Pro Ala Asp Lys Ala Gly Phe
            260                 265                 270

Val Gly Cys Arg Val Ala Val Thr Val Phe Leu Tyr Phe Leu Thr Thr
            275                 280                 285

Asn Tyr Tyr Trp Ile Leu Val Glu Gly Leu Tyr Leu His Ser Leu Ile
        290                 295                 300

Phe Met Ala Phe Phe Ser Glu Lys Lys Tyr Leu Trp Gly Phe Thr Leu
305                 310                 315                 320

Phe Gly Trp Gly Leu Pro Ala Val Phe Val Ala Val Trp Val Thr Val
                325                 330                 335

Arg Ala Thr Leu Ala Asn Thr Glu Cys Trp Asp Leu Ser Ser Gly Asn
            340                 345                 350

Lys Lys Trp Ile Ile Gln Val Pro Ile Leu Ala Ala Ile Val Val Asn
            355                 360                 365

Phe Ile Leu Phe Ile Asn Ile Ile Arg Val Leu Ala Thr Lys Leu Arg
        370                 375                 380

Glu Thr Asn Ala Gly Arg Cys Asp Thr Arg Gln Gln Tyr Arg Lys Leu
385                 390                 395                 400

Leu Lys Ser Thr Leu Val Leu Met Pro Leu Phe Gly Val His Tyr Ile
                405                 410                 415

Val Phe Met Ala Thr Pro Tyr Thr Glu Val Ser Gly Ile Leu Trp Gln
            420                 425                 430

Val Gln Met His Tyr Glu Met Leu Phe Asn Ser Phe Gln Gly Phe Phe
        435                 440                 445

Val Ala Ile Ile Tyr Cys Phe Cys Asn Gly Glu Val Gln Ala Glu Ile
450                 455                 460

Lys Lys Ser Trp Ser Arg Trp Thr Leu Ala Leu Asp Phe Lys Arg Lys
465                 470                 475                 480

Ala Arg Ser Gly Ser Ser Thr Tyr Ser Tyr Gly Pro Met Val Ser His
            485                 490                 495

Thr Ser Val Thr Asn Val Gly Pro Arg Gly Gly Leu Ala Leu Ser Leu
            500                 505                 510

Ser Pro Arg Leu Ala Pro Gly Ala Gly Ala Ser Ala Asn Gly His His
            515                 520                 525

Gln Leu Pro Gly Tyr Val Lys His Gly Ser Ile Ser Glu Asn Ser Leu
530                 535                 540

Pro Ser Ser Gly Pro Glu Pro Gly Thr Lys Asp Asp Gly Tyr Leu Asn
545                 550                 555                 560

Gly Ser Gly Leu Tyr Glu Pro Met Val Gly Glu Gln Pro Pro Pro Leu
                565                 570                 575

Leu Glu Glu Glu Arg Glu Thr Val Met
                580                 585
```

( 2 ) INFORMATION FOR SEQ ID NO: 7:

( i ) SEQUENCE CHARACTERISTICS:
        ( A ) LENGTH: 482 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i i i ) ANTI-SENSE: NO (v i) ORIGINAL SOURCE:
    (A) ORGANISM: Sus scrofa (x i) SEQUENCE DESCRIPTION: SEQ ID NO: 7:

| Met | Arg | Phe | Thr | Leu | Thr | Arg | Trp | Cys | Leu | Thr | Leu | Phe | Ile | Phe | Leu |
| 1 | | | | 5 | | | | | 10 | | | | | | 15 |
| Asn | Arg | Pro | Leu | Pro | Val | Leu | Pro | Asp | Ser | Ala | Asp | Gly | Ala | His | Thr |
| | | | | 20 | | | | | 25 | | | | | 30 | |
| Pro | Thr | Leu | Glu | Pro | Glu | Pro | Phe | Leu | Tyr | Ile | Leu | Gly | Lys | Gln | Arg |
| | | | 35 | | | | | 40 | | | | | 45 | | |
| Met | Leu | Glu | Ala | Gln | His | Arg | Cys | Tyr | Asp | Arg | Met | Gln | Lys | Leu | Pro |
| | 50 | | | | | 55 | | | | | 60 | | | | |
| Pro | Tyr | Gln | Gly | Glu | Gly | Leu | Tyr | Cys | Asn | Arg | Thr | Trp | Asp | Gly | Trp |
| 65 | | | | | 70 | | | | | 75 | | | | | 80 |
| Ser | Cys | Trp | Asp | Asp | Thr | Pro | Ala | Gly | Val | Leu | Ala | Glu | Gln | Tyr | Cys |
| | | | | 85 | | | | | 90 | | | | | 95 | |
| Pro | Asp | Tyr | Phe | Pro | Asp | Phe | Asp | Ala | Ala | Glu | Lys | Val | Thr | Lys | Tyr |
| | | | 100 | | | | | 105 | | | | | 110 | | |
| Cys | Gly | Glu | Asp | Gly | Asp | Trp | Tyr | Arg | His | Pro | Glu | Ser | Asn | Ile | Ser |
| | | | 115 | | | | | 120 | | | | | 125 | | |
| Trp | Ser | Asn | Tyr | Thr | Met | Cys | Asn | Ala | Phe | Thr | Pro | Asp | Lys | Leu | Gln |
| | 130 | | | | | 135 | | | | | 140 | | | | |
| Asn | Ala | Tyr | Ile | Leu | Tyr | Tyr | Leu | Ala | Ile | Val | Gly | His | Ser | Leu | Ser |
| 145 | | | | | 150 | | | | | 155 | | | | | 160 |
| Ile | Leu | Thr | Leu | Leu | Ile | Ser | Leu | Gly | Ile | Phe | Met | Phe | Leu | Arg | Ser |
| | | | | 165 | | | | | 170 | | | | | 175 | |
| Ile | Ser | Cys | Gln | Arg | Val | Thr | Leu | His | Lys | Asn | Met | Phe | Leu | Thr | Tyr |
| | | | 180 | | | | | 185 | | | | | 190 | | |
| Val | Leu | Asn | Ser | Ile | Ile | Ile | Ile | Val | His | Leu | Val | Val | Ile | Val | Pro |
| | | 195 | | | | | 200 | | | | | 205 | | | |
| Asn | Gly | Glu | Leu | Val | Lys | Arg | Asp | Pro | Pro | Ile | Cys | Lys | Val | Leu | His |
| | 210 | | | | | 215 | | | | | 220 | | | | |
| Phe | Phe | His | Gln | Tyr | Met | Met | Ser | Cys | Asn | Tyr | Phe | Trp | Met | Leu | Cys |
| 225 | | | | | 230 | | | | | 235 | | | | | 240 |
| Glu | Gly | Val | Tyr | Leu | His | Thr | Leu | Ile | Val | Val | Ser | Val | Phe | Ala | Glu |
| | | | | 245 | | | | | 250 | | | | | 255 | |
| Gly | Gln | Arg | Leu | Trp | Trp | Tyr | His | Val | Leu | Gly | Trp | Gly | Phe | Pro | Leu |
| | | | 260 | | | | | 265 | | | | | 270 | | |
| Ile | Pro | Thr | Thr | Ala | His | Ala | Ile | Thr | Arg | Ala | Val | Leu | Phe | Asn | Asp |
| | | 275 | | | | | 280 | | | | | 285 | | | |
| Asn | Cys | Trp | Leu | Ser | Val | Asp | Thr | Asn | Leu | Leu | Tyr | Ile | Ile | His | Gly |
| | 290 | | | | | 295 | | | | | 300 | | | | |
| Pro | Val | Met | Ala | Ala | Leu | Val | Val | Asn | Phe | Phe | Phe | Leu | Leu | Asn | Ile |
| 305 | | | | | 310 | | | | | 315 | | | | | 320 |
| Leu | Arg | Val | Leu | Val | Lys | Lys | Leu | Lys | Glu | Ser | Gln | Glu | Ala | Glu | Ser |
| | | | | 325 | | | | | 330 | | | | | 335 | |
| His | Met | Tyr | Leu | Lys | Ala | Val | Arg | Ala | Thr | Leu | Ile | Leu | Val | Pro | Leu |
| | | | 340 | | | | | 345 | | | | | 350 | | |
| Leu | Gly | Val | Gln | Phe | Val | Val | Leu | Pro | Trp | Arg | Pro | Ser | Thr | Pro | Leu |
| | | 355 | | | | | 360 | | | | | 365 | | | |
| Leu | Gly | Lys | Ile | Tyr | Asp | Tyr | Val | Val | His | Ser | Leu | Ile | His | Phe | Gln |
| | 370 | | | | | 375 | | | | | 380 | | | | |
| Gly | Phe | Phe | Val | Ala | Ile | Ile | Tyr | Cys | Phe | Cys | Asn | His | Glu | Val | Gln |
| 385 | | | | | 390 | | | | | 395 | | | | | 400 |

```
Gly Ala Leu Lys Arg Gln Trp Asn Gln Tyr Gln Ala Gln Arg Trp Ala
            405                 410                 415
Gly Arg Arg Ser Thr Arg Ala Ala Asn Ala Ala Ala Ala Thr Ala Ala
            420                 425                 430
Ala Ala Ala Ala Leu Ala Glu Thr Val Glu Ile Pro Val Tyr Ile Cys
            435                 440                 445
His Gln Glu Pro Arg Glu Glu Pro Ala Gly Glu Glu Pro Val Val Glu
            450                 455                 460
Val Glu Gly Val Glu Val Ile Ala Met Glu Val Leu Glu Gln Glu Thr
            465                 470                 475                 480
Ser Ala
```

( 2 ) INFORMATION FOR SEQ ID NO: 8:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v i ) ORIGINAL SOURCE:
        ( A ) ORGANISM: Homo sapiens ( x i ) SEQUENCE DESCRIPTION: SEQ ID NO: 8:

```
Arg Leu Ala Lys
 1
```

( 2 ) INFORMATION FOR SEQ ID NO: 9:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i i i ) ANTI-SENSE: NO ( v i ) ORIGINAL SOURCE:
        ( A ) ORGANISM: Homo sapiens ( x i ) SEQUENCE DESCRIPTION: SEQ ID NO: 9:

```
Lys Ala Leu Lys
 1
```

What is claimed is:

1. An isolated glucagonlike peptide-1 (GLP-1) receptor polypeptide having the amino acid sequence of a naturally occurring mammalian GLP-1 receptor encoded by a cDNA molecule isolated from a pancreatic islet library and comprising a nucleotide sequence selected from the group consisting of:

SEQ ID NO: 1;
SEQ ID NO: 3; and
the sequence of a cDNA molecule capable of specifically hybridizing with a probe having the sequence of the complement of SEQ ID NO: 1 or SEQ ID NO: 3 under conditions of relaxed stringency, wherein a probe having the sequence of the complement of SEQ ID NO: 1 will specifically identify a cDNA comprising the sequence shown in SEQ ID NO: 3 in a human cDNA library, said receptor polypeptide capable of binding GLP-1 with a $K_D$ of less than 100 nM.

2. A GLP-1 receptor polypeptide according to claim 1 of rat or human origin.

3. An isolated nucleic acid molecule which comprises a nucleotide sequence encoding a GLP-1 receptor polypeptide according to claim 1.

4. A nucleic acid molecule according to claim 3, which comprises the DNA sequence shown in SEQ ID NO: 1.

5. A nucleic acid molecule according to claim 3 which comprises the partial DNA sequence shown in SEQ ID NO: 3.

6. A recombinant expression vector which comprises a DNA insert having the sequence of a nucleic acid molecule according to claim 3.

7. A cultured eukaryotic cell containing a recombinant expression vector according to claim 6.

8. A cultured eukaryotic cell containing a DNA construct comprising the sequence of a nucleic acid molecule according to claim 4 integrated in its genome.

9. A method of screening for agonists or enhancers of GLP-1 activity, the method comprising the steps of incubating a GLP-1 receptor polypeptide according to claim 1 with a substance suspected to be an agonist or enhancer of GLP-1 activity; subsequently incubating said receptor polypeptide with GLP-1; and detecting the binding of said GLP-1 to said receptor polypeptide.

10. A method of screening for agonists or enhancers of GLP-1 activity, the method comprising the steps of incubating GLP-1 with a substance suspected to be an agonist or enhancer of GLP-1 activity; subsequently incubating said GLP-1 with the GLP-1 receptor polypeptide of claim 1; and detecting the binding of said GLP-1 to said receptor polypeptide.

11. An isolated DNA molecule comprising the nucleotide sequence shown in SEQ ID NO: 3.

* * * * *